US008372049B2

(12) United States Patent
Jaeb et al.

(10) Patent No.: US 8,372,049 B2
(45) Date of Patent: Feb. 12, 2013

(54) DRESSING AND METHOD FOR APPLYING REDUCED PRESSURE TO AND COLLECTING AND STORING FLUID FROM A TISSUE SITE

(75) Inventors: Jonathan Paul Jaeb, Boerne, TX (US); Richard Daniel John Coulthard, Verwood (GB); Timothy Mark Robinson, Basingstoke (GB); Christopher Brian Locke, Bournemouth (GB); Aldan Marcus Tout, Ringwood (GB)

(73) Assignee: KCI Licensing, Inc., San Antonio, TX (US)

( * ) Notice: Subject to any disclaimer, the term of this patent is extended or adjusted under 35 U.S.C. 154(b) by 701 days.

(21) Appl. No.: 12/398,891

(22) Filed: Mar. 5, 2009

(65) Prior Publication Data

US 2009/0227969 A1 Sep. 10, 2009

Related U.S. Application Data

(60) Provisional application No. 61/034,013, filed on Mar. 5, 2008, provisional application No. 61/049,028, filed on Apr. 30, 2008.

(51) Int. Cl.
*A61M 1/00* (2006.01)
(52) U.S. Cl. .................. 604/313; 604/315; 604/543
(58) Field of Classification Search .................. 604/313, 604/315, 543
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,172,808 A * | 3/1965 | Heinz et al. | ..................... 602/42 |
| 3,367,332 A | 2/1968 | Groves | |
| 3,376,868 A | 4/1968 | Mondiadis | |
| 3,520,300 A | 7/1970 | Flower, Jr. | |
| 3,568,675 A | 3/1971 | Harvey | |
| 3,648,692 A | 3/1972 | Wheeler | |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986);pp. 94-96 (copy and certified translation).

(Continued)

*Primary Examiner* — Susan Su

(57) ABSTRACT

A reduced pressure treatment system includes a reduced pressure source and a reduced pressure dressing. The dressing includes an interface layer adapted to be positioned at a tissue site and an absorbent layer in fluid communication with the interface layer to absorb liquid from at least one of the interface layer and the tissue site. A diverter layer is positioned adjacent the absorbent layer, and the diverter layer includes a plurality of apertures in fluid communication with the absorbent layer to distribute a reduced pressure to the absorbent layer. A cover is positioned over the diverter layer to maintain the reduced pressure at the tissue site.

15 Claims, 16 Drawing Sheets

U.S. PATENT DOCUMENTS

| | | | |
|---|---|---|---|
| 3,682,180 A | 8/1972 | McFarlane | |
| 3,742,952 A | 7/1973 | Magers et al. | |
| 3,774,611 A | 11/1973 | Tussey et al. | |
| 3,779,243 A | 12/1973 | Tussey et al. | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,141,361 A | 2/1979 | Snyder | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,529,402 A | 7/1985 | Weilbacher et al. | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,652 A | 5/1987 | Weilbacher | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,961,493 A * | 10/1990 | Kaihatsu | 206/0.5 |
| 4,969,880 A | 11/1990 | Zamierowski | |
| 4,981,474 A | 1/1991 | Bopp et al. | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,112,323 A | 5/1992 | Winkler et al. | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,329 A | 8/1994 | Croquevielle | |
| 5,342,376 A | 8/1994 | Ruff | |
| 5,344,415 A | 9/1994 | DeBusk et al. | |
| 5,358,494 A | 10/1994 | Svedman | |
| 5,387,207 A * | 2/1995 | Dyer et al. | 604/369 |
| 5,437,622 A | 8/1995 | Carion | |
| 5,437,651 A | 8/1995 | Todd et al. | |
| 5,527,293 A | 6/1996 | Zamierowski | |
| 5,549,584 A * | 8/1996 | Gross | 604/313 |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,710,233 A | 1/1998 | Meckel et al. | |
| 5,941,863 A | 8/1999 | Guidotti et al. | |
| 6,071,267 A | 6/2000 | Zamierowski | |
| 6,135,116 A | 10/2000 | Vogel et al. | |
| 6,174,306 B1 | 1/2001 | Fleischmann | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,458,109 B1 | 10/2002 | Henley et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,626,891 B2 | 9/2003 | Ohmstede | |
| 6,814,079 B2 | 11/2004 | Heaton et al. | |
| 6,979,324 B2 | 12/2005 | Bybordi et al. | |
| 7,070,584 B2 | 7/2006 | Johnson et al. | |
| 7,569,742 B2 | 8/2009 | Haggstrom | |
| 2002/0065494 A1 | 5/2002 | Lockwood et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0150720 A1 | 10/2002 | Howard et al. | |
| 2002/0161346 A1 | 10/2002 | Lockwood et al. | |
| 2002/0183702 A1 | 12/2002 | Henley et al. | |
| 2002/0198504 A1 | 12/2002 | Risk, Jr. et al. | |
| 2004/0030304 A1 * | 2/2004 | Hunt et al. | 604/317 |
| 2004/0064132 A1 | 4/2004 | Boehringer et al. | |
| 2004/0186239 A1 * | 9/2004 | Qin et al. | 525/327.4 |
| 2005/0070858 A1 | 3/2005 | Lockwood et al. | |
| 2005/0137539 A1 | 6/2005 | Biggie et al. | |
| 2005/0143694 A1 * | 6/2005 | Schmidt et al. | 604/304 |
| 2005/0256437 A1 * | 11/2005 | Silcock et al. | 602/48 |
| 2005/0261642 A1 | 11/2005 | Weston | |
| 2005/0261643 A1 | 11/2005 | Bybordi et al. | |
| 2006/0271020 A1 | 11/2006 | Huang et al. | |
| 2007/0027414 A1 * | 2/2007 | Hoffman et al. | 602/2 |
| 2007/0078366 A1 * | 4/2007 | Haggstrom et al. | 602/53 |
| 2007/0185426 A1 * | 8/2007 | Ambrosio et al. | 602/43 |
| 2007/0225663 A1 | 9/2007 | Watt et al. | |
| 2007/0265585 A1 | 11/2007 | Joshi et al. | |
| 2008/0119802 A1 | 5/2008 | Riesinger | |
| 2008/0243044 A1 | 10/2008 | Hunt et al. | |
| 2009/0227969 A1 | 9/2009 | Jaeb et al. | |
| 2009/0264807 A1 | 10/2009 | Haggstrom | |
| 2009/0326488 A1 | 12/2009 | Budig et al. | |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |

| | | |
|---|---|---|
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 01/85248 A1 | 11/2001 |
| WO | WO 03/045492 A1 | 6/2003 |
| WO | WO 2005/105176 A1 | 11/2005 |
| WO | WO 2007/133618 A2 | 11/2007 |
| WO | WO 2008/041926 A1 | 4/2008 |
| WO | WO 2008/100440 A | 9/2008 |
| WO | WO 2008/104609 A | 9/2008 |
| WO | WO 2009/066105 A1 | 5/2009 |
| WO | WO 2009/066106 A1 | 5/2009 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bidirectional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax, "Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988)("Solovev Abstract").

NPD 1000 Negative Pressure Wound Therapy System, Kalypto Medical, pp. 1-4.

Partial International Search Report date mailed Jul. 31, 2009; PCT International Application No. PCT/US2009/036222.

International Search Report and Written Opinion date mailed Dec. 15, 2009; PCT International Application No. PCT/US2009/036222.

International Search Report and Written Opinion date mailed Feb. 24, 2010; PCT/US2009/057182.

International Search Report and Written Opinion date mailed Jan. 5, 2010; PCT International Application No. PCT/US2009/057130.
Partial International Search Report date mailed Jul. 31, 2009 for PCT International Application No. PCT/US2009/036217.
International Search Report and Written Opinion date mailed May 31, 2010 for PCT Application No. PCT/US2009/064364.
Response filed Oct. 20, 2011 for U.S. Appl. No. 12/398,904.
Interview Summary date mailed Oct. 27, 2011 for U.S. Appl. No. 12/398,904.
Non-Final Office Action date mailed Jul. 20, 2011 for U.S. Appl. No. 12/398,904.

* cited by examiner

_US 8,372,049 B2_

DRESSING AND METHOD FOR APPLYING REDUCED PRESSURE TO AND COLLECTING AND STORING FLUID FROM A TISSUE SITE

CROSS-REFERENCE TO RELATED APPLICATIONS

This application claims the benefit of U.S. Provisional Application No. 61/034,013 filed Mar. 5, 2008, and U.S. Provisional Application No. 61/049,028 filed Apr. 30, 2008, both of which are hereby incorporated by reference.

BACKGROUND OF THE INVENTION

1. Field of the Invention

The present invention relates generally to tissue treatment systems and in particular to dressings for distributing reduced pressure to and collecting and storing fluid from a tissue site.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue. The porous pad may be incorporated into a dressing having other components that facilitate treatment.

SUMMARY

The problems presented by existing collection canisters are solved by the systems and methods of the illustrative embodiments described herein. In one illustrative embodiment, a reduced pressure treatment system is provided. The reduced pressure treatment system includes a reduced pressure source and a reduced pressure dressing. The dressing includes an interface layer adapted to be positioned at a tissue site and an absorbent layer in fluid communication with the interface layer to absorb liquid from at least one of the interface layer and the tissue site. A diverter layer is positioned between the absorbent layer and the reduced pressure source, and the diverter layer includes a plurality of apertures in fluid communication with the absorbent layer to distribute a reduced pressure to the absorbent layer. A cover is positioned over the diverter layer to maintain the reduced pressure at the tissue site.

In another illustrative embodiment, a reduced pressure treatment system includes a reduced pressure source and a dressing in fluid communication with the reduced pressure source. The dressing includes an interface layer adapted to be positioned at a tissue site and capable of distributing a reduced pressure from the reduced pressure source to the tissue site. An absorbent layer is in fluid communication with the interface layer to absorb liquid from the interface layer and the tissue site. A cover is provided to maintain the reduced pressure at the tissue site, and a liquid-air separator is positioned between the absorbent layer and the cover to inhibit liquid from exiting the dressing.

In another illustrative embodiment, a reduced pressure dressing adapted to distribute a reduced pressure to a tissue site is provided. The dressing includes an interface layer adapted to be positioned at the tissue site and an absorbent layer in fluid communication with the interface layer to absorb liquid from at least one of the interface layer and the tissue site. A diverter layer is adjacent the absorbent layer, and the diverter layer is formed from a substantially gas-impermeable material. The diverter layer includes a plurality of apertures in fluid communication with the absorbent layer to increase an amount of time that the absorbent layer is able to distribute reduced pressure. A cover is positioned over the diverter layer to maintain the reduced pressure at the tissue site.

In still another illustrative embodiment, a reduced pressure dressing adapted to distribute a reduced pressure to a tissue site includes an interface layer adapted to be positioned at the tissue site. A first manifold layer is positioned in fluid communication with the interface layer to distribute the reduced pressure to the interface layer. An absorbent layer is in fluid communication with the first manifold layer to absorb liquid from at least one of the first manifold layer, the interface layer, and the tissue site. A diverter layer is positioned adjacent the absorbent layer, the diverter layer formed from a substantially gas-impermeable material and including a plurality of spaced apertures in fluid communication with the absorbent layer. A second manifold layer is positioned in fluid communication with the diverter layer to distribute the reduced pressure to the diverter layer. A cover is provided to maintain the reduced pressure at the tissue site, and the cover includes an aperture through which the reduced pressure is adapted to be delivered to the dressing. A liquid-air separator is positioned between the second manifold and the cover to inhibit liquid from exiting the dressing.

In yet another illustrative embodiment, a method is provided for collecting fluid in a dressing positioned at a tissue site. The method includes applying a reduced pressure to the tissue site through the dressing, absorbing liquid from the tissue site, and storing the liquid in the dressing. The method further includes preventing the liquid from exiting the dressing.

In another illustrative embodiment, a reduced pressure dressing kit is provided that includes dressing components. The dressing components include an interface layer, an absorbent layer, a diverter layer, and a cover. The dressing components are capable of being assembled to manifold reduced pressure at a tissue site and to collect fluid from the tissue site.

In still another illustrative embodiment, a reduced pressure treatment system includes a reduced pressure source and a dressing in fluid communication with the reduced pressure source. The dressing includes an absorbent layer in fluid communication with a tissue site to absorb liquid from the tissue site as a reduced pressure is applied to the dressing by the reduced pressure source. A cover is provided and is capable of maintaining the reduced pressure within the dressing and is capable of expanding from an unexpanded position to an expanded position as the liquid is absorbed by the absorbent layer.

In another embodiment, a reduced pressure dressing adapted to distribute a reduced pressure to a tissue site is provided. The dressing includes an interface layer adapted to be positioned at the tissue site, and an absorbent layer in fluid communication with the interface layer to absorb liquid from at least one of the interface layer and the tissue site. A diverter layer is adjacent the absorbent layer, and the diverter layer is formed from a substantially gas-impermeable material. The diverter layer includes a surface area smaller than a surface area of the absorbent layer such that flow is directed around at least one perimeter edge of the diverter layer. A cover is positioned over the diverter layer to maintain the reduced pressure at the tissue site.

In another illustrative embodiment, a reduced pressure dressing adapted to distribute a reduced pressure to a tissue site includes an interface layer adapted to be positioned at the tissue site. An absorbent layer is in fluid communication with the interface layer to absorb liquid from at least one of the interface layer and the tissue site. A diverter layer is in fluid communication with the absorbent layer, and the diverter layer is formed from a substantially gas-permeable, liquid impermeable material. A cover is positioned over the diverter layer to maintain the reduced pressure at the tissue site.

Other objects, features, and advantages of the illustrative embodiments will become apparent with reference to the drawings and detailed description that follow.

DETAILED DESCRIPTION OF ILLUSTRATIVE EMBODIMENTS

Figure 1:
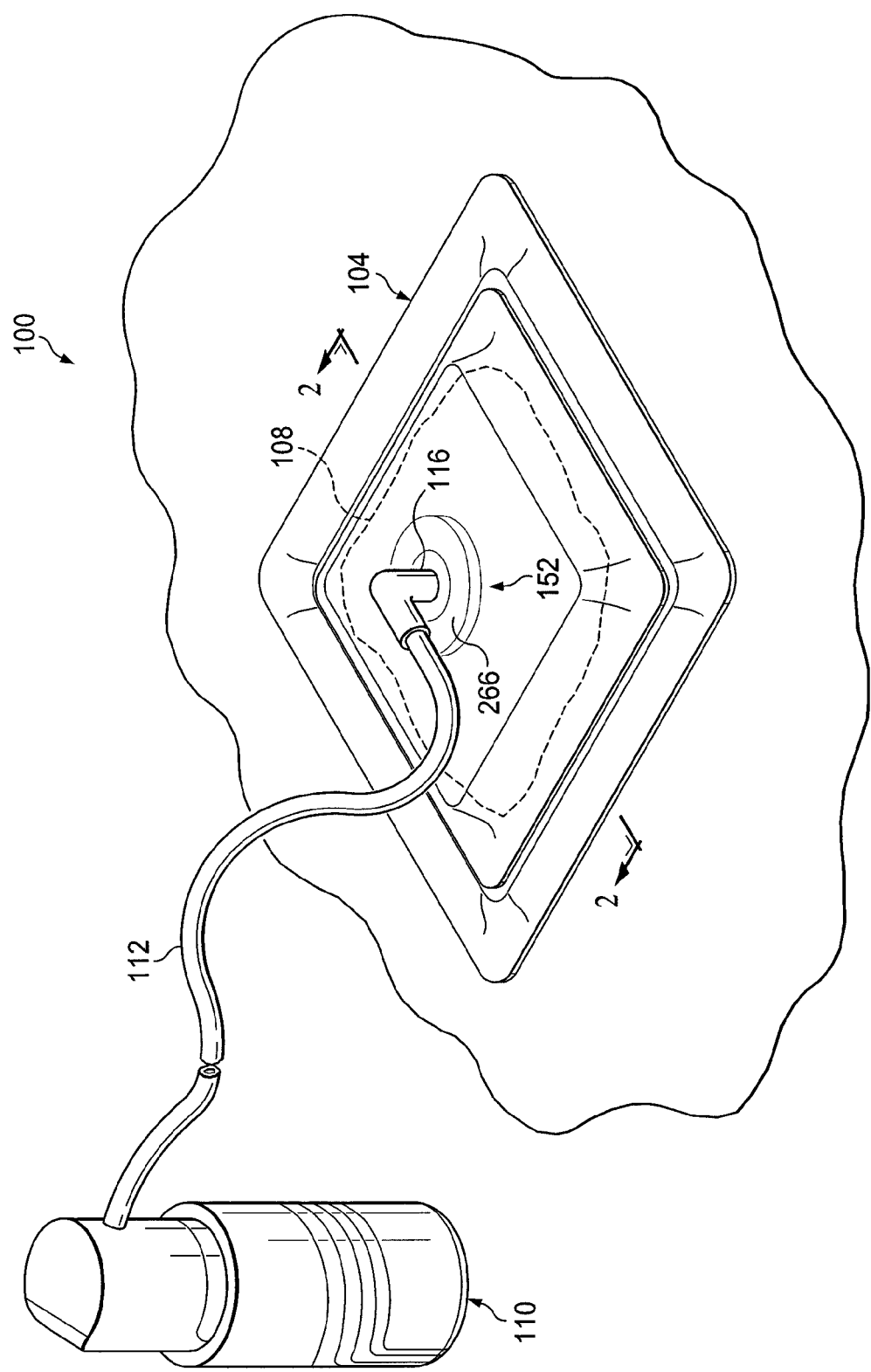
FIG. 1 illustrates a perspective view of a reduced pressure treatment system according to an illustrative embodiment, the reduced pressure treatment system having a dressing positioned at a tissue site.

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Reduced pressure treatment systems are often applied to large, highly exudating wounds present on patients undergoing acute or chronic care, as well as other severe wounds that are not readily susceptible to healing without application of reduced pressure. Low-severity wounds that are smaller in volume and produce less exudate have generally been treated using advanced dressings instead of reduced pressure treatment. These advanced dressings, however, are not adapted for use with reduced pressure and are subject to several drawbacks when used in conjunction with reduced pressure. For example, these current dressings may fail to make optimal use of fluid storage capacity in the dressing. Additionally, existing dressings are not configured to adequately transmit reduced pressure, especially as the dressings begin to absorb and store fluid.

Currently, the use of reduced pressure treatment is not considered a viable or affordable option for low-severity wounds due to the manpower required to monitor and change system components, the requirement for trained medical personnel overseeing treatment, and the cost of treatment. For example, the complexity of current reduced pressure treatment systems limits the ability of a person with little or no specialized knowledge from administering such treatment to oneself or others. The size of current reduced pressure treatment systems also impairs the mobility of both the treatment system and the person to whom the treatment is being applied. For example, current reduced pressure treatment systems require the use of a separate canister that stores exudate or other liquid from the tissue site. Current reduced pressure treatment systems are also typically non-disposable after each treatment, and require electrical components or other powered devices in order to apply the reduced pressure used in treatment.

Reduced Pressure Dressing

Referring to FIG. 1, a reduced pressure treatment system 100 according to an illustrative embodiment includes a reduced pressure dressing 104 positioned at a tissue site 108 of a patient. The reduced pressure dressing 104 is fluidly connected to a reduced pressure source 110 by a conduit 112. The conduit 112 may fluidly communicate with the reduced pressure dressing 104 through a tubing adapter 116. In the embodiment illustrated in FIG. 1, the reduced pressure source 110 is a manually-actuated pump such as, for example, a compressible bellows pump. In another implementation, the reduced pressure source 110 may be a reduced pressure or vacuum pump driven by a motor. In another embodiment, the reduced pressure source 110 may be a powered micropump such as, for example, a piezoelectric disc pump, or alternatively a peristaltic pump. In still another embodiment, the reduced pressure source 110 may be a wall suction port such as are available in hospitals and other medical facilities.

The reduced pressure source 110 may be housed within a reduced pressure treatment unit, which may also contain sensors, processing units, alarm indicators, memory, databases, software, display units, and user interfaces that further facilitate the application of reduced pressure treatment to the tissue site 108. In one example, a sensor or switch (not shown) may be disposed at or near the reduced pressure source 110 to determine a source pressure generated by the reduced pressure source 110. The sensor may communicate with a processing unit that monitors and controls the reduced pressure that is delivered by the reduced pressure source 110. Delivery of reduced pressure to the reduced pressure dressing 104 and tissue site 108 encourages new tissue growth by maintaining drainage of exudate from the tissue site, increasing blood flow to tissues surrounding the tissue site, and creating microstrain at the tissue site.

Figure 2:
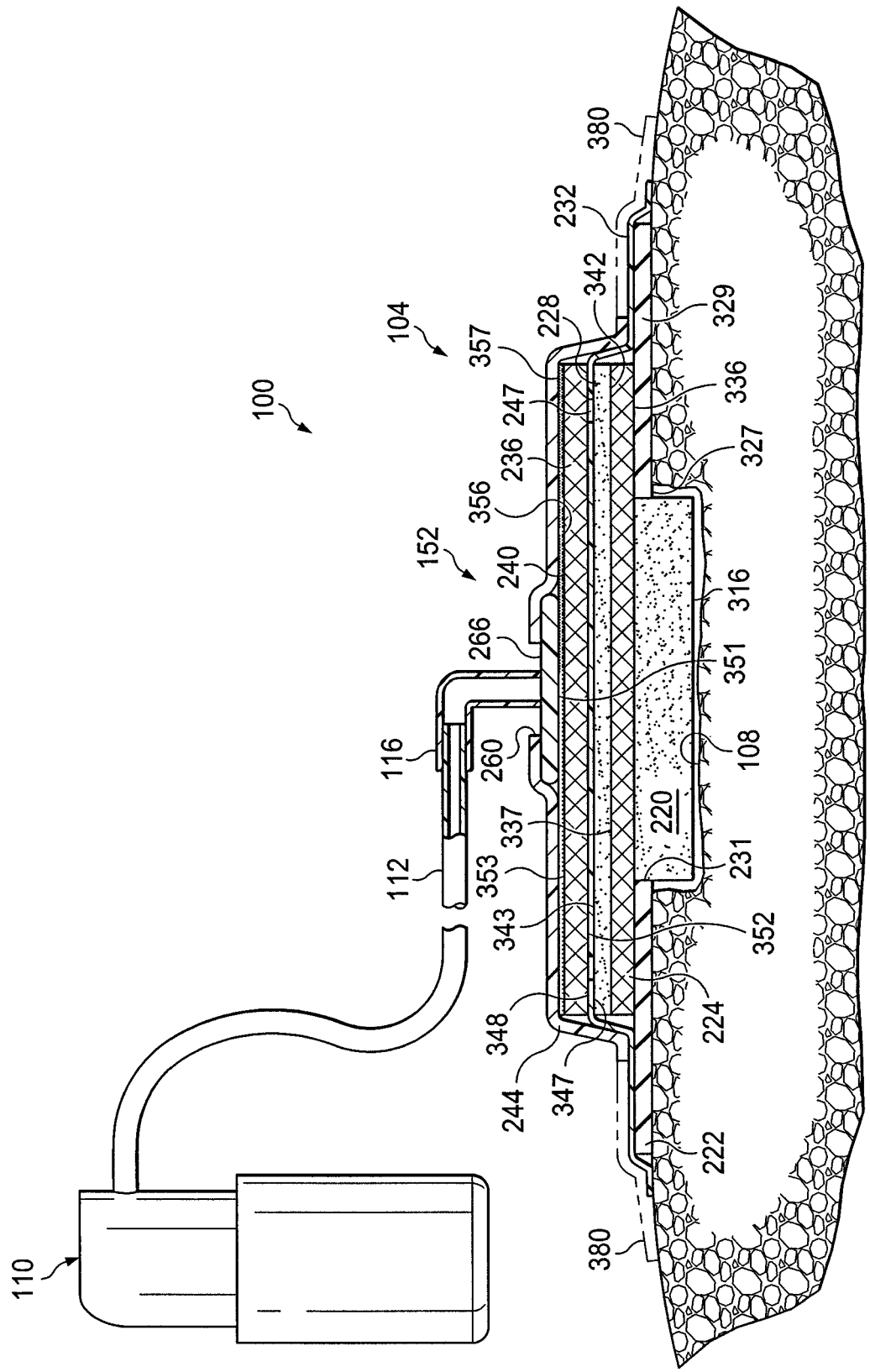
FIG. 2 depicts a cross-sectional front view of the dressing of FIG. 1 taken at 2-2.
Figure 3:
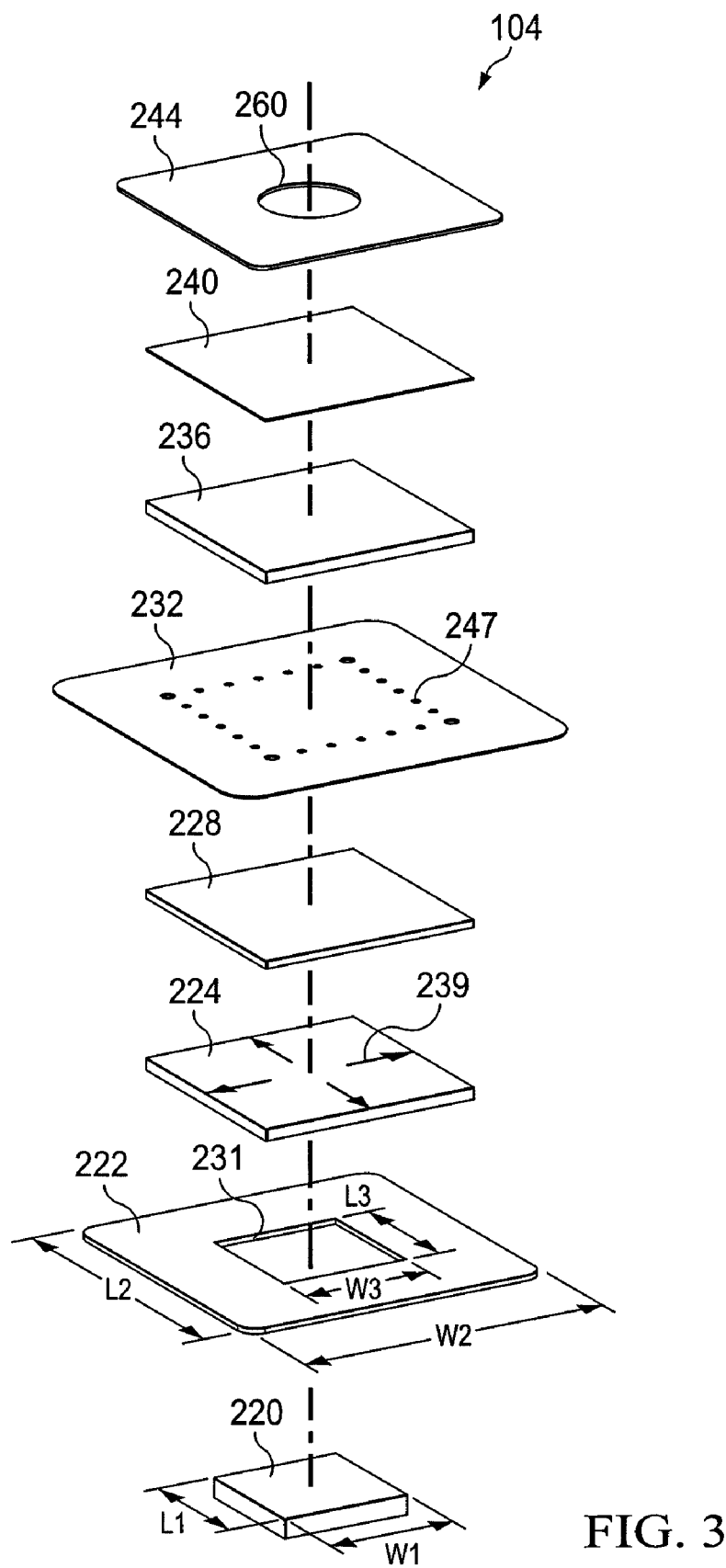
FIG. 3 illustrates an exploded perspective view of the dressing of FIG. 1.

Referring to FIGS. 2 and 3, the reduced pressure dressing 104 includes an interface layer 220 adapted to be positioned at the tissue site 108, and a seal layer 222 to seal the reduced pressure dressing 104 around the tissue site 108. A first manifold layer 224 is in fluid communication with the interface layer 220 to distribute the reduced pressure to the interface layer 220 and the tissue site 108. An absorbent layer 228 is positioned in fluid communication with the first manifold layer 224 to absorb liquid from at least one of the first manifold layer 224, the interface layer 220, and the tissue site 108. A diverter layer 232 is positioned adjacent the absorbent layer 228. A second manifold layer 236 is positioned in fluid communication with the diverter layer 232, and a liquid-air separator 240 is positioned adjacent the second manifold layer 236. A cover 244, or drape, is positioned adjacent the liquid-air separator 240.

The interface layer 220 of the reduced pressure dressing 104 is adapted to contact the tissue site 108. The interface layer 220 may be partially or fully in contact with the tissue site 108 being treated by the reduced pressure dressing 104. When the tissue site 108 is a wound, the interface layer 220 may partially or fully fill the wound.

The interface layer 220 may be any size, shape, or thickness depending on a variety of factors, such as the type of treatment being implemented or the nature and size of the tissue site 108. For example, the size and shape of the interface layer 220 may be customized by a user to cover a particular portion of the tissue site 108, or to fill or partially fill the tissue site 108. Although the interface layer 220 illustrated in FIG. 3 has a square shape, the interface layer 220 may be shaped as a circle, oval, polygon, an irregular shape, or any other shape.

In one illustrative embodiment, the interface layer 220 is a foam material that functions as a manifold to provide reduced pressure to the tissue site 108 when the interface layer 220 is in contact with or near the tissue site 108. The foam material may be either hydrophobic or hydrophilic. In one non-limiting example, the interface layer 220 is an open-cell, reticulated polyurethane foam such as GranuFoam® dressing available from Kinetic Concepts, Inc. of San Antonio, Tex.

In the example in which the interface layer 220 is made from a hydrophilic material, the interface layer 220 also functions to wick fluid away from the tissue site 108, while continuing to provide reduced pressure to the tissue site 108 as a manifold. The wicking properties of the interface layer 220 draw fluid away from the tissue site 108 by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The interface layer 220 may further promote granulation at the tissue site 108 when a reduced pressure is applied through the reduced pressure dressing 104. For example, any or all of the surfaces of the interface layer 220 may have an uneven, coarse, or jagged profile that causes microstrains and stresses at the tissue site 108 when reduced pressure is applied through the interface layer 220. These microstrains and stresses have been shown to increase new tissue growth.

In one embodiment, the interface layer 220 may be constructed from bioresorbable materials that do not have to be removed from a patient's body following use of the reduced pressure dressing 104. Suitable bioresorbable materials may include, without limitation, a polymeric blend of polylactic acid (PLA) and polyglycolic acid (PGA). The polymeric blend may also include without limitation polycarbonates, polyfumarates, and capralactones. The interface layer 220 may further serve as a scaffold for new cell-growth, or a scaffold material may be used in conjunction with the interface layer 220 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The seal layer 222 of the reduced pressure dressing 104 includes an aperture or opening 231 and provides a seal around the tissue site 108. The seal layer 222 may serve as a gasket around a portion of the tissue site 108 to prevent reduced pressure applied to the reduced pressure dressing 104 from leaking out of the reduced pressure dressing 104. The seal layer 222 may also be used to secure the interface layer 220 at the tissue site 108. If the cover 244 is applied to the tissue surrounding the tissue site 108 with wrinkles in the cover 244, then the seal layer 222 assists in maintaining in the wrinkled areas of the cover 244.

The seal layer 222 may be any size and thickness capable of providing a seal around the tissue site 108. In the example of FIG. 2, a length, L2, and a width, W2, of the seal layer 222 are greater than a length, L1, and a width, W1, of the interface layer 220, respectively. Thus, portions of the seal layer 222 extend past the edges of the interface layer 220. These portions may contact the tissue surrounding the tissue site 108 directly, thereby providing a seal around the tissue site 108 and the interface layer 220.

While the seal layer 222 illustrated in FIG. 3 has a square shape, the seal layer 222 may also have any other shape that provides a seal around the tissue site 108 or the interface layer 220. Non-limiting examples of other shapes include a circle, oval, any polygonal shape, an irregular shape, or a shape that is customized to contour to the tissue surrounding the tissue site 108 or the interface layer 220.

The seal layer 222 may be made from any material that is capable of sealing around the treated portion of the tissue site 108. In one illustrative embodiment, the seal layer 222 may include or be made from a hydrogel. The seal layer 222 may also include either or both of a hydrocolloid or silicon.

Although the seal layer 222 is shown as being disposed adjacent to the interface layer 220, the seal layer 222 may be positioned adjacent or between any of the layers in the reduced pressure dressing 104. Additional details regarding the positioning of the seal layer 222 are discussed in more detail below with reference to FIG. 2.

The reduced pressure dressing 104 also includes a first manifold layer 224 for distributing the reduced pressure to and withdrawing liquid, such as exudate, from the interface layer 220. When the seal layer 222 is positioned adjacent the interface layer 220, liquid may be withdrawn from the tissue site 108 through the aperture 231. As a reduced pressure is applied to the reduced pressure dressing 104, the liquid is wicked from the tissue site 108 by the interface layer 220 and drawn through the aperture 231 of the seal layer 222 by the first manifold layer 224.

In one embodiment, a length, L3, and a width, W3, of the aperture 231 is less than the length, L1, and the width, W1, of the interface layer 220. However, in other embodiments, particularly in those embodiments in which one or more other layers are disposed between the seal layer 222 and the interface layer 220, the length, L3, and the width, W3, of the aperture 231 may be equal to or larger than the length, L1, and the width, W1, of the interface layer 220. While the aperture 231 illustrated in FIG. 3 has a square shape, the aperture 231 may instead have any other shape that allows the seal layer 222 to provide a seal while facilitating the passage of liquid from the tissue site 108.

The first manifold layer 224 may have any size, shape, or thickness. For example, the size and shape of the first manifold layer 224 may be customized to provide differing levels of utilization of the absorbent layer 228. The size and shape of the first manifold layer 224 may also be customized based on the size and shape of other components in the reduced pressure dressing 104, such as the size and shape of the interface layer 220, the seal layer 222, the aperture 231, the absorbent layer 228, or other layers in the reduced pressure dressing 104.

The first manifold layer 224 is a biocompatible, porous material that is capable of distributing reduced pressure to the tissue site 108. The first manifold layer 224 may be made from foam, gauze, felted mat, or any other material suited to a particular biological application. The first manifold layer 224 includes a plurality of flow channels or pathways to facilitate distribution of reduced pressure or fluids to or from the tissue site 108. In one embodiment, the first manifold layer 224 is a porous foam and includes a plurality of interconnected cells or pores that act as flow channels. The porous foam may be a polyurethane, open-cell, reticulated foam such as GranuFoam® dressing. If an open-cell foam is used, the porosity may be about 400 to 600 microns or any other porosity capable of adequately manifolding reduced pressure. The flow channels allow fluid communication throughout the portion of first manifold layer 224 having open cells. The cells and flow channels may be uniform in shape and size, or may include patterned or random variations in shape and size. Variations in the shape and size of the cells of the first manifold layer 224 result in variations in the flow channels, and such characteristics may be used to alter the flow characteristics of fluid through first manifold layer 224. The first manifold layer 224 may be either hydrophobic or hydrophilic. In one embodiment, the first manifold layer 224 may be made from the same material as the interface layer 220.

In one embodiment, the first manifold layer 224 may be made from a material that expands upon contact with a liquid, such as exudate from the tissue site 108, such that the first manifold layer 224 will fill a wound site or otherwise contact the tissue site 108. In this embodiment, the first manifold layer 224 may enable the interface layer 220 to be removed, thereby simplifying the construction and reducing the thickness or profile of the reduced pressure dressing 104.

The absorbent layer 228 of the reduced pressure dressing 104 is disposed adjacent the first manifold layer 224 for receiving and absorbing the liquids distributed by the first manifold layer 224. The first manifold layer 224 facilitates the migration of liquid from the tissue site 108 radially outward toward the edges of the first manifold layer 224, as indicated generally by the multi-directional arrows 239 so that the liquid is distributed more uniformly across the absorbent layer 228. The absorbent layer 228 will retain more liquid if the liquid is more uniformly distributed across the surface of the absorbent layer 228.

As used herein, a "surface area" of a layer refers to an area measurement of the layer as may be determined in a plane that is positioned adjacent to or in contact with other layers. In the example illustrated in FIG. 3, the surface areas of the first manifold layer 224 and the absorbent layer 228 are determined by multiplying the lengths and widths of the respective layers, the lengths and widths being measured in a plane substantially parallel to the plane containing the length, L3, and the width, W3, of the aperture 231.

A surface area (defined as L3×W3) of the aperture 231 in FIG. 3 may be less than a surface area of the first manifold layer 224 and a surface area of the absorbent layer 228. If the first manifold layer 224 failed to distribute the liquid radially toward the edges of the first manifold layer 224, then the absorbent layer 228 would primarily absorb liquid in a portion of the absorbent layer 228 having a same size as the aperture 231. However, because the first manifold layer 224 is capable of radially distributing liquid from the tissue site 108 in the directions indicated by the multi-directional arrows 239, a larger surface area of the absorbent layer 228 is exposed to the liquid, and the absorbent layer 228 can store a larger volume of fluid. While the reduced pressure dressing 104 is designed primarily for use with reduced pressure, the distribution of liquid from the tissue site 108 in the directions indicated by the multi-directional arrows 239 may occur during the application of or in the absence of reduced pressure. A more complete utilization of the absorbent layer 228 may be achieved using the first manifold layer 224 even when reduced pressure is not being applied to the reduced pressure dressing 104.

The absorbent layer 228 is adapted to absorb liquid, such as exudate, from the tissue site 108 via the interface layer 220 and the first manifold layer 224 through the aperture 231 of the seal layer 222. The absorbent layer 228 is also adapted to manifold and transfer reduced pressure through those layers to the tissue site 108. The absorbent layer 228 may be made from any material capable of absorbing liquid, such as exudate from the tissue site 108. In one embodiment, the absorbent layer 228 may be made from a super absorbent fiber. The super absorbent fibers may hold onto or bond to the liquid in conjunction with a physical or chemical change to the fibers. In one non-limiting example, the super absorbent fiber may include the Super Absorbent Fiber (SAF) material from Technical Absorbents®, Ltd. The absorbent layer 228 may be a sheet or mat of fibrous material in which the fibers absorb liquid from the tissue site 108. The structure of the absorbent layer 228 that contains the fibers may be either woven or non-woven. The fibers in the absorbent layer 228 may gel upon contact with the liquid, thereby trapping the liquid. Spaces or voids between the fibers may allow a reduced pressure that is applied to the reduced pressure dressing 104 to be transferred within and through the absorbent layer 228. In one embodiment, the fiber density of fibers in the absorbent layer 228 may be approximately 1.4 grams per millimeter.

The absorbent layer 228 may have any size, shape, or thickness. If additional liquid storage capacity is desired for the reduced pressure dressing 104, then a larger or thicker absorbent layer 228 may be used. In another example, the size and thickness of the absorbent layer 228 may be reduced for space-saving, convenience, compactness, or cost considerations.

The reduced pressure dressing 104 may also include a diverter layer 232 disposed adjacent to the absorbent layer 228, a second manifold layer 236 disposed adjacent the diverter layer 232, and a liquid-air separator 240 disposed adjacent the second manifold layer 236. The diverter layer 232 includes a plurality of holes 247 though which reduced pressure from the reduced pressure source 110 (see FIG. 1) is applied. The reduced pressure is distributed to the diverter layer 232 by the second manifold layer 236. The holes 247 may be arranged in a pattern for applying the reduced pressure to portions of the absorbent layer 228 to enhance the capability of the absorbent layer 228 to continue transferring the reduced pressure to the tissue site 108 as it absorbs more fluid from the tissue site 108. In the embodiment illustrated in FIG. 3, the plurality of holes 247 are positioned in a pattern around a peripheral portion of the diverter layer 232 away from the center of the diverter layer 232 such that the reduced pressure is applied to the absorbent layer 228 away from a center region of the absorbent layer 228. The diverter layer 232 acts in conjunction with the first manifold layer 224 to ensure that the absorption capabilities and absorption efficiency of the absorbent layer 228 is increased relative to an absorbent layer that is not used in conjunction with a diverter layer. By providing better distribution of liquid throughout the absorbent layer 228, the diverter layer 232 also increases an amount of time over which the absorbent layer 228 is capable of manifolding reduced pressure in the dressing 104.

The diverter layer 232 may be made from any material that enhances the reduced pressure transmission and storage capabilities of an adjacent absorbent layer. For example, the diverter layer 247 may be made from a material that is substantially impermeable to liquid and gas. Alternatively, the material from which the diverter layer 232 is made may instead have a predetermined moisture vapor transfer rate that is consistent with gas permeability. In either example, the diverter layer 232 may still include a pattern of holes for transmitting a greater volume of liquid or gas than that permitted by the gas-permeable material of which the diverter layer 232 is constructed. It should be noted, however, that permeability of the diverter layer 232 to gas but not liquid may result in increased transmission of reduced pressure through the dressing while still directing liquid flow around or near the perimeter of the diverter layer 232.

In the embodiment illustrated in FIG. 3, the reduced pressure creates fluid flow through the holes 247. The fluid flow through holes 247 directs liquid pulled into the absorbent layer 228 away from a center region of the absorbent layer 228. The presence of holes 247 and the fluid flow through the holes 247 may also lessen the absorption rate of liquid in the center region of the absorbent layer 228 and allow the absorbent layer 228 to absorb liquid over a larger area. Thus, the gas and liquid are not limited only to traveling through the center of the absorbent layer 228 or other layers that may be disposed closer to the tissue site 108 than the diverter layer 232. Because both the gas and liquid are directed radially outward toward the edges of the absorbent layer 228, a greater portion of absorbent material is exposed to the liquid from the tissue site 108, and a larger portion of the absorbent layer 228 may therefore be used to store or trap a greater volume of the liquid.

The fuller utilization of the absorbent layer 228 allows for the reduced pressure dressing 104 to be used for a longer period of time without having to dispose the reduced pressure dressing 104. The need to distribute gas and liquid toward the edges of the absorbent layer 228 may be even greater in the presence of reduced pressure due to the speed at which liquid may flow away from the tissue site 108 through the reduced pressure dressing 104.

The diverter layer 232 has primarily been described as assisting in diverting reduced pressure or fluid flow to a perimeter region of the absorbent layer 228. Alternatively, the diverter layer 232 could instead be configured to assist in diverting reduced pressure to any particular region, i.e. a target region, of the absorbent layer 228 to encourage liquid absorption within the target region. For example, if a tissue site and a dressing were of a configuration that naturally resulted in liquid collection in a perimeter region of a particular absorbent layer, then a diverter layer could be configured to encourage liquid collection within the center region of the absorbent layer. In this particular example, the center region would be the target region.

Referring still to FIGS. 2 and 3, the second manifold layer 236 distributes the reduced pressure more uniformly across the surface of the diverter layer 232. The second manifold layer 236 may be made from any material capable of distributing or manifolding fluid. In one example, the second manifold layer 236 may be made from a same or similar material as the first manifold layer 224. In this example, the second manifold layer 236 may include a plurality of interconnected cells that form a porous foam. The second manifold layer 236 may also collect liquid, such as exudate, from the tissue site 108 that is not absorbed by the absorbent layer 228. The second manifold layer 236 may have any size, shape, or thickness.

In one embodiment of the reduced pressure dressing 104, the liquid-air separator 240 may be a hydrophobic filter that inhibits or prevents passage of liquids through the liquid-air separator 240. Alternatively, the liquid-air separator 240 may be a gravity-based barrier system, or a device that includes a hydrophilic surface to encourage condensation or other separation of liquid from a fluid stream when the fluid stream passes over the surface. Other examples of liquid-air separators 240 may include sintered metals, sintered nylons, or any other material or device that is capable of separating liquid from a fluid stream, or that is otherwise capable of inhibiting or preventing the passage of liquid while allowing the passage of gases.

By restraining or preventing the flow of liquid, the liquid-air separator 240 prevents liquid from reaching the tubing adapter 116 or conduit 112 (see FIG. 1). By preventing liquid from reaching the conduit 112, the liquid-air separator 240 also prevents the liquid from reaching the reduced pressure source 110.

The liquid-air separator 240 may prevent the passage of reduced pressure to the tissue site 108 when the liquid-air separator 240 becomes saturated, clogged, blocked, and/or wetted with liquid from the tissue site 108. The liquid-air separator 240 may also prevent the passage of reduced pressure to the tissue site 108 when a layer that abuts the liquid-air separator 240 becomes saturated with liquid. For example, if the absorbent layer 228 abutted the liquid-air separator 240 in a particular embodiment, the saturation of the absorbent layer 228 with liquid may cause the liquid-air separator 240 to prevent the passage of reduced pressure. The presence of the diverter layer 232 between the liquid-air separator 240 and the absorbent layer 228 prolongs the period of time before the liquid-air separator 240 blocks the passage of reduced pressure.

The liquid-air separator 240 may have any size, shape, or thickness. In one example, the liquid-air separator 240 may be smaller than other layers in the reduced pressure dressing 104 due to cost considerations. The liquid-air separator 240 may also be wider than the tubing adapter 116 and an aperture 260 in the cover 244 so that liquid from the tissue site 108 cannot reach the tubing adapter 116 or the aperture 260.

The cover 244 of the reduced pressure dressing 104 covers at least a portion of the reduced pressure dressing 104. In one embodiment, the cover 244 may fully cover the multiple layers of the reduced pressure dressing 104. In this embodiment, the cover 244 may secure or assist in securing the reduced pressure dressing 104 to the tissue site 108 and in maintaining a seal around the tissue site 108. In this respect, both the cover 244 and the seal layer 222 may work together to create a seal around the tissue site 108. The cover 244 may also provide a protective barrier for the reduced pressure dressing 104 and the tissue site 108.

In the embodiment illustrated in FIGS. 2 and 3, the cover 244 may cover and secure components and layers between the cover 244 and the diverter layer 232. In this embodiment, the cover 244 may be secured either adhesively or otherwise to the diverter layer 232. The diverter layer 232, which may be made from a similar material as the cover 244, is then secured to either or both of the seal layer 222 and the tissue at or near the tissue site 108. The diverter layer 232 in this embodiment secures and seals the components and layers beneath the diverter layer 232 at the tissue site 108.

In one embodiment, the cover 244 may be an adhesive drape. The adhesion of the cover 244 may be due to the nature of the material with which the cover 244 is made, or may be due to an adhesive layer disposed on a surface of the cover 244. Any portion of the cover 244 may include adhesive. For example, an entire tissue facing side of the cover 244 may include adhesive. When provided with adhesive, the cover 244 may adhere to at least a portion of the tubing adapter 116, the tissue surrounding the tissue site 108, or any layer or component of the reduced pressure dressing 104. In another embodiment, only the peripheral portions of the tissue facing side of the cover 244 may include adhesive. In this particular case, the adhesive-covered peripheral portions may be adapted to adhere to any of the diverter layer 232, the seal layer 222, and the tissue surrounding the tissue site 108.

In still another embodiment, the cover 244 may be designed such that the cover 244 will not adhere to wet surfaces, but will adhere to dry surfaces. Thus, when applying the cover 244, the cover 244 will not stick to moistened gloves or hands, thereby permitting easier handling of the cover 244 until the cover 244 is placed on a dry tissue site, such as a dry periwound area. The cover 244 may be any size, shape, or thickness. In one example, the cover 244 may be larger than any layer or components of the reduced pressure dressing 104. In another example, the size of the seal layer 222 may be larger than the size of the cover 244.

Reduced pressure may be applied to the plurality of layers of the reduced pressure dressing 104 via the aperture 260 in the cover 244. In the example of FIGS. 2 and 3, the aperture 260 is shown to be centrally located on the cover 244. However, the aperture 260 may be located anywhere on the cover 244, including a peripheral portion of the cover 244 that is adjacent to an edge of cover 244. Although the aperture 260 is shown to be circular, the aperture 260 may have any shape. In one example, the shape of the aperture is adapted to contour to one or more portions of the tubing adapter 116.

The tubing adapter 116 provides an interface between conduit 112 and the reduced pressure dressing 104. In particular, the tubing adapter 116 fluidly communicates with the conduit 112 such that the conduit 112 transfers reduced pressure to the reduced pressure dressing 104 and the tissue site 108 via the tubing adapter 116.

Referring to FIGS. 1 and 2, the tubing adapter 116 may be a conventional connector pad that is adapted to abut or be partially disposed within the aperture 260. Alternatively, the tubing adapter 116 may have a low profile dome shape, or the tubing adapter 116 may be any other shape. The low profile of the tubing adapter 116 may help to keep the reduced pressure dressing 104 compact and convenient for use by a user. The tubing adapter 116 includes a flange 266, which is disposed around the periphery of the tubing adapter 116. In the embodiment illustrated in FIGS. 2 and 3, the tissue facing side of the cover 244 near the aperture 260 may be adapted to adhere to the flange 266 such that the tubing adapter 116 is secured to at least one layer or component of the reduced pressure dressing 104.

Although not shown in FIGS. 2 and 3, in one embodiment the reduced pressure dressing 104 includes an odor filter. The odor filter retains or prevents odor from exiting the reduced pressure dressing 104. The odor filter may be a carbon odor filter, which may include charcoal. In one example, the odor filter is a charcoal cloth. The odor filter may be positioned anywhere in the reduced pressure dressing 104 such as, for example, between the cover 244 and the liquid-air separator 240.

The reduced pressure dressing 104 may further include an indicator (not shown) to alert a user when the reduced pressure dressing 104 has reached a full liquid storage capacity and needs to be removed from the tissue site 108. In one embodiment, the indicator may be a chemical or other substance that is capable of changing visual appearance or some other characteristic in the presence of moisture. For example, an indicator may be placed in one of the layers between the cover 244 and the absorbent layer 228 such that the indicator undergoes a visible color change when liquid has fully saturated the absorbent layer and is pulled through the absorbent layer into contact with the indicator. In one embodiment, the indicator may be a part of the liquid-air separator 240. The indicator may instead be a part of a separate indicator layer that is positioned anywhere in the dressing to signal the presence of moisture in a particular area. The indicator may cooperate with another layer of the dressing that is transparent to allow a user to view the location at which the indicator is positioned.

Although the cover 244, the liquid-air separator 240, the manifolds 224 and 236, the diverter layer 232, the absorbent layer 228, the seal layer 222, and the interface layer 220 have substantially square shapes in FIG. 3, each of these components, as well as other layers disclosed herein with respect to other embodiments, may have any shape as required to provide adequate reduced pressure therapy to the tissue site 108. For example, these components and layers may be polygonal, rectangular, circular, ovular, an irregular shape, a customized shape, or any other shape.

While the various layers of the reduced pressure dressing 104 have been described as being "adjacent" to other layers, the term "adjacent" may refer to the layers being immediately adjacent, or alternatively that the layers may be positioned with other intervening layers in between. The term "layer" generally refers to portions or regions of the dressing that have different material properties or functions than other portions or regions of the dressing (i.e. other layers). The term "layer" is not meant to be spatially limiting however. The properties and functions associated with a particular layer may be combined with the properties and functions of another layer such that a single layer having multiple and different properties and functions is created. More specifically, for example, two or more layers may be physically or chemically bonded or combined to create a single layer without affecting the original material properties or functions of the original components. Conversely, a particular layer of the dressings described herein may be broken into two or more layers that each have similar properties or functions.

Referring more specifically to FIG. 2, the specific arrangement of the multiple layers of the reduced pressure dressing 104 is described in more detail. A tissue facing side 316 of the interface layer 220 is shown to be abutting the tissue site 108. In one example, the tissue facing side 316 of the interface layer 220 has an uneven surface that promotes granulation of the tissue site 108 when reduced pressure is applied through the interface layer 220. The uneven surface include a fibrous surface that causes microstresses and strains on the tissue site 108.

The seal layer 222 may be disposed anywhere between the cover 244 and interface layer 220, including between the absorbent layer 228 and interface layer 220. In the example of FIG. 2, the seal layer 222 is disposed between the first manifold layer 224 and the interface layer 220 such that a portion of a tissue facing side 327 of the seal layer 222 abuts the interface layer 220. In particular, the tissue facing side of an inner edge of the seal layer 222 that forms the aperture 231 abuts the interface layer 220.

The seal layer 222 also includes overhanging portions 329, which extend past the edges of the interface layer 220. The overhanging portions 329 may be adapted to adhere or otherwise contact the tissue site 108 such that a seal is created at a portion of the tissue site 108. For example, the overhanging portion 329 may adhere or otherwise contact a periwound area surrounding a wound site such that a seal is created at the wound site.

The first manifold layer 224 may also be disposed anywhere in the reduced pressure dressing 104. In one example, the first manifold layer 224 is disposed between the interface layer 220 and the absorbent layer 228. In the non-limiting example of FIG. 3, the first manifold layer 224 is disposed between the seal layer 222 and the absorbent layer 228. In particular, a portion of a tissue facing side 336 of the first manifold layer 224 abuts the aperture 231 of the seal layer 222. In this example, a drape facing side 337 of the first manifold layer 224 abuts the absorbent layer 228.

In the embodiment illustrated in FIG. 2, the absorbent layer 228 is shown to be disposed between the diverter layer 232 and the first manifold layer 224. A tissue facing side 342 of the absorbent layer 228 abuts the first manifold layer 224. A drape facing side 343 of the absorbent layer 228 abuts the diverter layer 232. In one example, the diverter layer 232 may be disposed between the absorbent layer 228 and the cover 244. A tissue facing side 347 of the diverter layer 232 abuts the absorbent layer 228. A drape facing side 348 of the diverter layer 232 abuts the second manifold layer 236.

The second manifold layer 236 may be disposed between the absorbent layer 228 and the cover 244, or between the diverter layer 232 and the cover 244. In FIG. 2, the second manifold layer 236 is disposed between the liquid-air separator 240 and the diverter layer 232. A tissue facing side 352 of the second manifold layer 236 abuts the diverter layer 232. A drape facing side 353 of the second manifold layer 236 abuts the liquid-air separator 240.

The liquid-air separator 240 may be disposed between the absorbent layer 228 and the cover 244, or between the second manifold layer 236 and the cover 244. In FIG. 2, a tissue facing side 356 of the liquid-air separator 240 abuts the second manifold layer 236. A portion of a drape facing side 357 of the liquid-air separator 240 abuts the tubing adapter 116.

A tissue facing side 351 of the tubing adapter 116 abuts the liquid-air separator 240. Also, a portion of the tubing adapter 116 is shown to protrude from an aperture in the cover 244. The flange 266 of the tubing adapter 116 is sandwiched between the cover 244 and the liquid-air separator 240 such that the cover 244 secures the tubing adapter 116 to at least one of the plurality of layers, such as the liquid-air separator 240. As illustrated in FIG. 2, the liquid-air separator 240 may be wider than the aperture 260 in the cover 244, and the second manifold layer 236 may be wider than the liquid-air separator 240.

The cover 244 may cover all or a part of the reduced pressure dressing 104. For example, the ends of the cover 244 may terminate at a location on the overhanging portions 329 of the seal layer 222. As indicated by the broken lines 380, the cover 244 may also terminate at a location on the tissue site 108.

Figure 4:
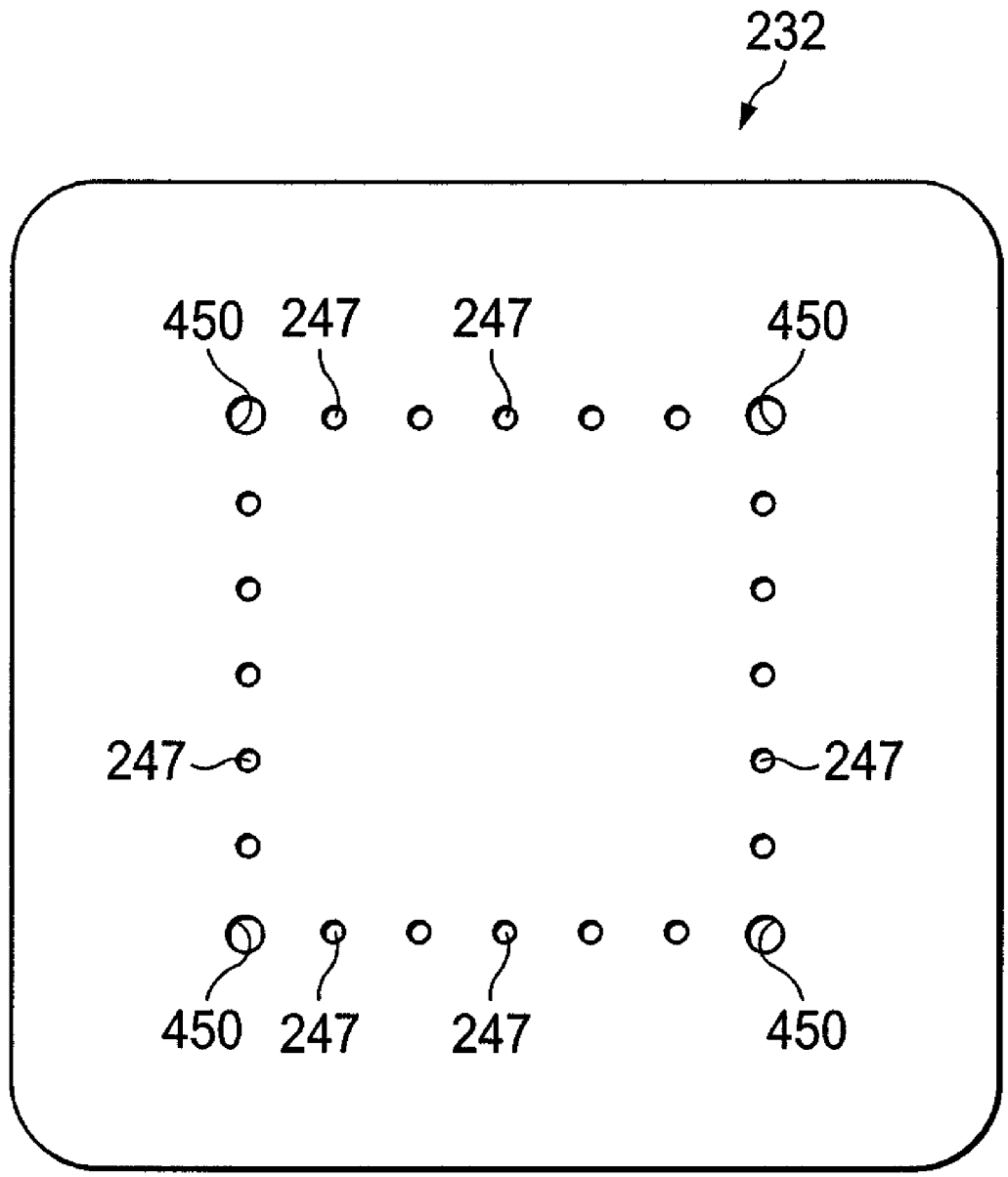
FIG. 4 depicts a top view of a diverter layer the dressing of FIG. 3.

Referring to FIG. 4, the diverter layer 232 includes a pattern of holes, or other apertures for applying the reduced pressure to portions of the absorbent layer 228 (not shown). The holes have different diameters. More specifically, the diameter of holes 450 are larger than the diameter of holes 247. In operation, the diverter layer 232 channels more reduced pressure to the corners of a square absorbent layer 228 to further enhance the transmission capability of the absorbent layer 228 because the corners are the last portion of the absorbent layer 228 to fill with liquid as liquid diffuses radially outward from the center of the absorbent layer 228.

Figure 5:
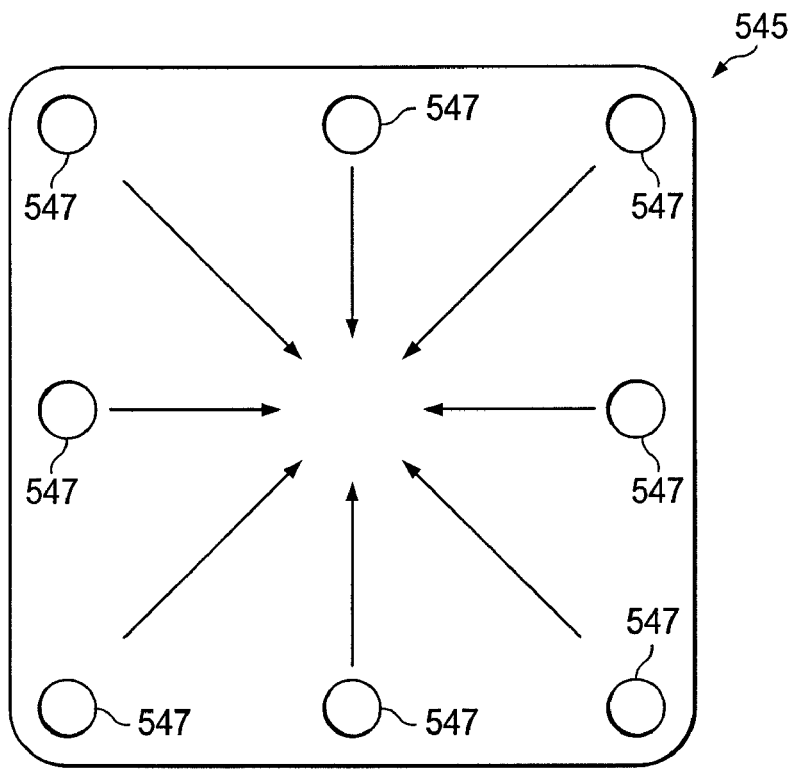
FIG. 5 illustrates a top view of a diverter layer according to an illustrative embodiment.
Figure 6:
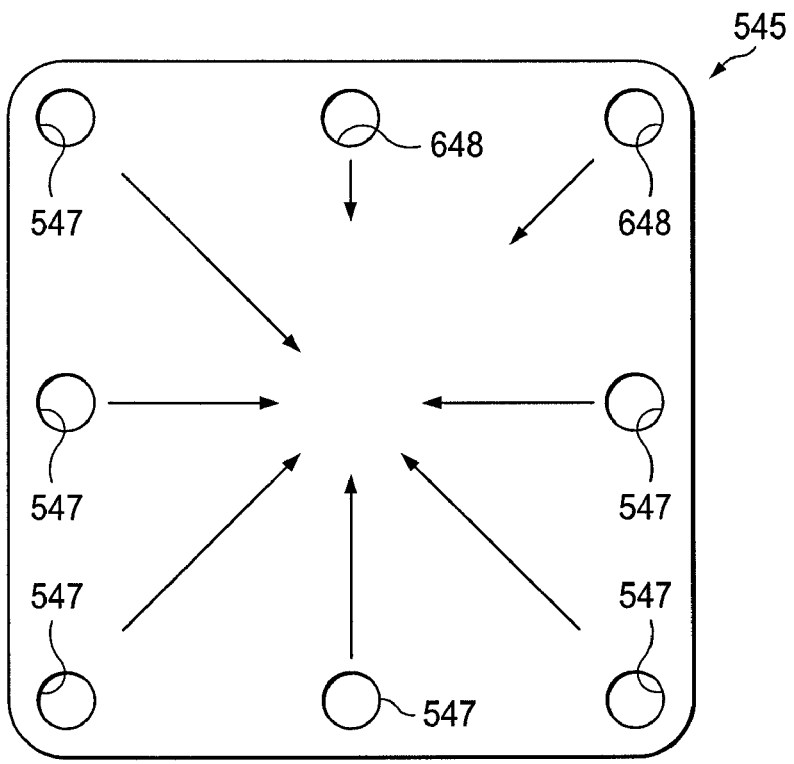
FIG. 6 depicts a top view of the diverter layer of FIG. 5.

Referring to FIGS. 5 and 6, a diverter layer 545 according to an illustrative embodiment may be made from any material that expands on contact with a liquid. For example, the diverter layer 545 may be made from a hydrogel. The diverter layer 545 may also include a hydrocolloid, silicon, or silicone material. The diverter layer 545 includes holes 547, or other apertures. The length of each of the arrows extending from each of the holes 547 represents the relative amount of flow or reduced pressure allowed through the holes. In FIG. 5, an equal amount of flow or reduced pressure is transferred through each of the holes 547.

In some reduced pressure applications, the tissue may produce more exudate at an area away from the center of the dressing. In these cases, a greater amount of liquid may pass through a portion of the holes 547 that are positioned over the main point of exudation. In the example of FIG. 6, the main point of exudation occurs nearer to holes 648. Thus, the holes 648 are shown to be smaller, swelling, or substantially closed off due to contact with liquid from the tissue site. The restriction of the holes 648 causes a preferential flow through the remaining holes 547, thereby equalizing flow across an adjacent absorbent layer in the dressing. In particular, the holes 547 of diverter layer 545 as shown in FIG. 6 transmit a greater amount of reduced pressure than the holes 648. By equalizing flow and reduced pressure in such a manner, an absorbent layer, such as absorbent layer 228 in FIGS. 2 and 3, may be more fully utilized no matter the location of the main point of exudation at the tissue site, or the pattern with which the liquid is absorbed by the absorbent layer.

Figure 7:
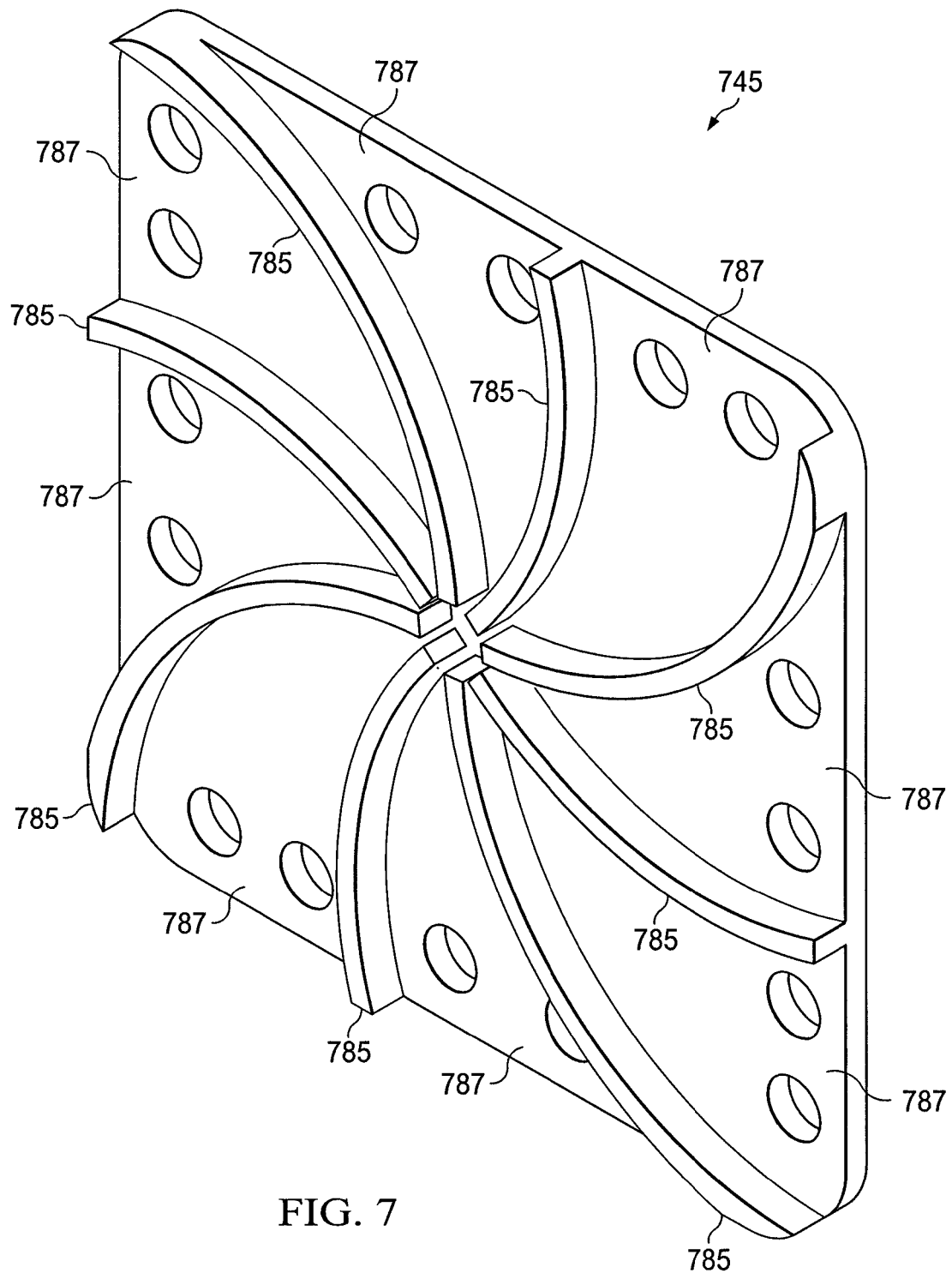
FIG. 7 illustrates a perspective view of a diverter layer according to an illustrative embodiment.
Figure 8:
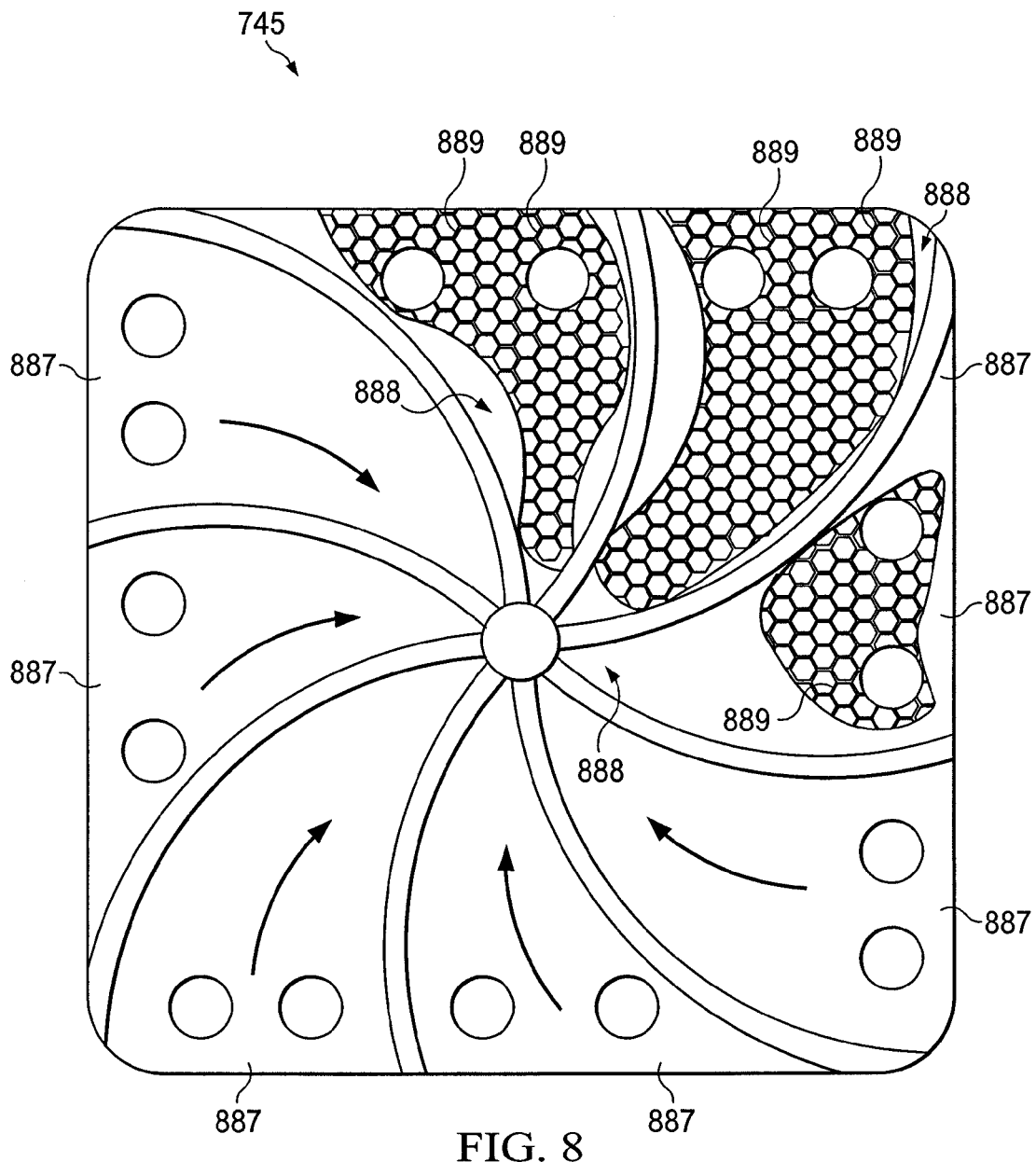
FIG. 8 depicts a top view of the diverter layer of FIG. 7.

Referring to FIGS. 7 and 8, a diverter layer 745 according to an illustrative embodiment includes a plurality of ridges 785 protruding from a surface of the diverter layer 745 and extending radially outward from the center to a periphery of the diverter layer 745 to form or define a plurality of channels 787 therebetween. The ridges 785 may be curved and may converge at a central portion of the diverter layer 745. The ridged face of the diverter 745 abuts an absorbent layer (not shown) so that the channels 787 are closed to form passages 887 and 888 (FIG. 8) extending radially between the center portion and periphery of the diverter layer 745. In FIG. 8, each of the passages 887 are shown to be unobstructed, and therefore a substantially equal amount of reduced pressure freely flows through each one. However, in some reduced pressure applications, liquid from the tissue site 108 (not shown) fills and obstructs the passages 888. This may occur, for example, when a main point of exudation from the tissue site is located away from the center of the dressing, including the diverter layer 745. Because a greater amount of liquid flows through the passages 888 than the passages 887, the passages 888 fill with the liquid and become obstructed by the saturated portions of the absorbent layer 228 abutting the passages 888 as indicated by shaded portions 889. Thus, as indicated by the arrows on the diverter layer 745, a greater amount of reduced pressure is applied through the passages 887 than the obstructed passages 888. The passages 887 then become a preferential path for the reduced pressure and fluid flow until all of the absorbent layer 228 adjacent the diverter layer 745 is saturated. By equalizing flow in such a manner, the absorbent layer 228 is more fully utilized regardless of the location of the main point of exudation on the tissue site, or the pattern with which the liquid is absorbed by the absorbent layer 228.

Figure 9:
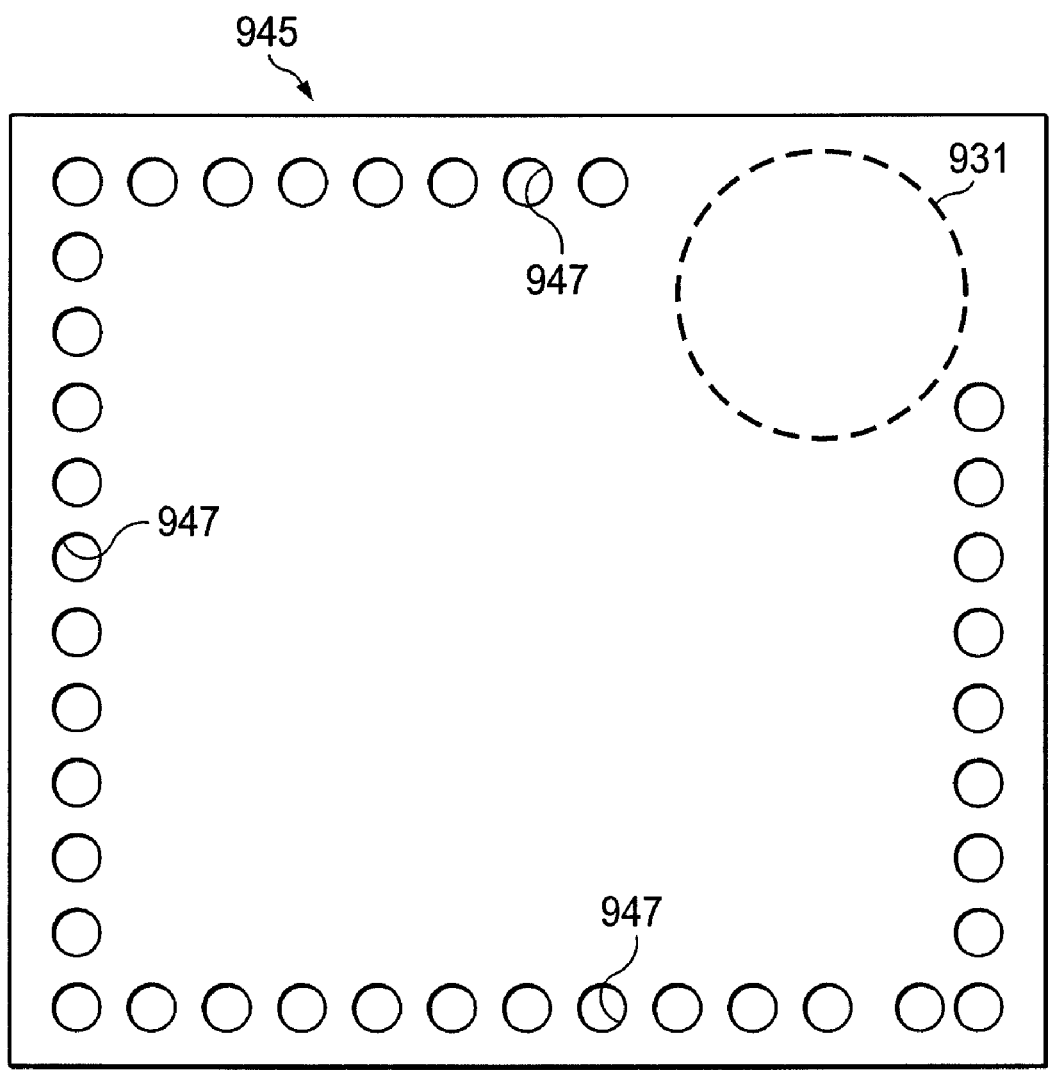
FIG. 9 illustrates a top view of a diverter layer according to an illustrative embodiment.

Referring to FIG. 9, a diverter layer 945 is shown according to an illustrative embodiment. The diverter layer 945 includes a pattern of holes 947, or other apertures around a periphery of the diverter layer 945. However, in contrast to the diverter layer 232 of FIGS. 2 and 3, the diverter layer 945 includes a portion 931 that does not include holes 947. The portion 931 is capable of being aligned with a tubing adapter (similar to tubing adapter 116) that is positioned off-center. Because reduced pressure is applied to the dressing via the tubing adapter, the presence of holes directly underneath the tubing adapter, even with one or more intervening layers, may result in a larger than desired portion of the reduced pressure being applied to the holes adjacent and underneath the tubing adapter. Eliminating holes in the portion 931 of the diverter layer 945 that is adjacent and underneath the tubing adapter applies the reduced pressure through all of the remaining holes 947 to more evenly distribute the reduced pressure to the absorbent layer 228.

While the diverter layers of FIGS. 4-9 have been illustrated and described as including substantially circular holes, the diverter layers may instead include apertures of any shape or size, including for example slots, slits, channels, perforations, or any other apertures. Alternatively, a diverter layer may be provided without apertures that instead is sized to be smaller in perimeter dimension and/or surface area than the absorbent layer. A diverter layer having a length or width less than a length or width of the absorbent layer would ensure fluid flow travels around perimeter edges of the diverter layer, thus having the same effect as placement of apertures near an edge of a larger diverter layer.

Figure 10:
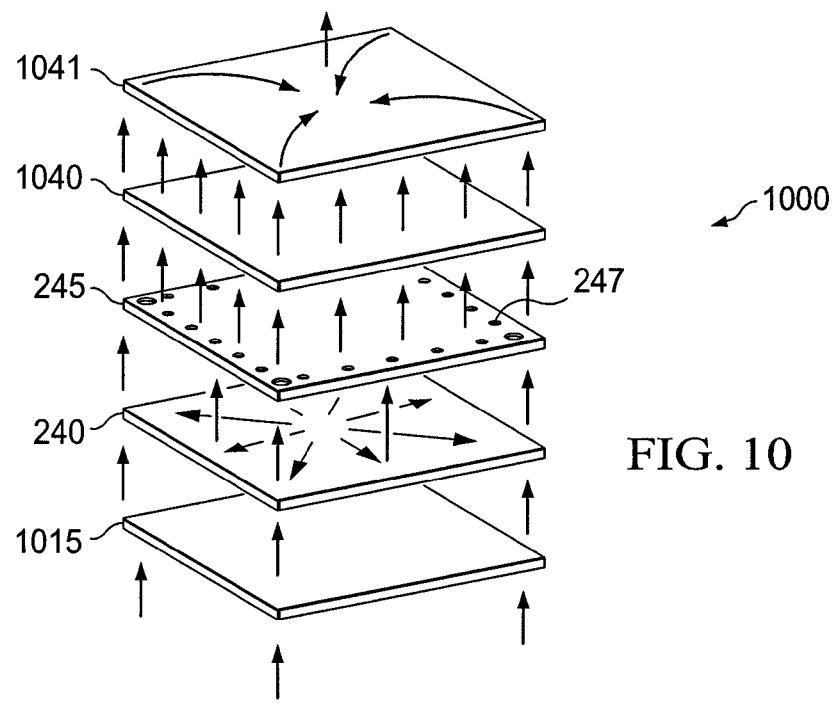
FIG. 10 depicts an exploded perspective view of a reduced pressure dressing according to an illustrative embodiment.

Referring to FIG. 10, a reduced pressure dressing 1000 is shown according to an illustrative embodiment. The reduced pressure dressing 1000 is similar to the reduced pressure dressing 104 of FIGS. 2 and 3. The reduced pressure dressing 1000 is not shown with the tubing adapter 116 or the cover 244 of FIGS. 2 and 3, but includes the absorbent layer 228 and the diverter layer 232. The reduced pressure dressing 1000 further includes a heat/moisture exchange (HME) foam 1015, which is a non-limiting example of the interface layer 220 in FIGS. 2 and 3. The HME foam 1015 may be a hydrophilic foam that wicks liquid from the tissue site 108. The HME foam 1015 may also distribute reduced pressure to the tissue site. In one example, the tissue-facing side of the HME foam 1015 has an uneven surface such that granulation is promoted at the tissue site 108 when reduced pressure is applied through the HME foam 1015. Each of the arrows in FIG. 10 represents the flow of either or both of gas or liquid when reduced pressure is applied to the reduced pressure dressing 1000. The arrows illustrate how the diverter layer 232 facilitates the distribution of gas and liquid throughout the reduced pressure dressing 1000 to more effectively utilize the absorbent layer 228. For example, the arrows show that the presence of the diverter layer 232 causes liquid to be drawn radially outward toward the edges of the absorbent layer 228 to more fully utilize the absorbent capacity of the absorbent layer 228.

The reduced pressure dressing 1000 also includes a second absorbent layer 1040 disposed adjacent the diverter layer 232 on a side opposite the first absorbent layer 228, and a second HME layer 1041 disposed adjacent the opposite side of the second absorbent layer 1040. The second HME layer 1041 may be an open-celled and/or hydrophilic foam. In one example, the HME layer 1041 is made of the same material as the HME foam 1015. Liquid from the tissue site 108 (not shown) is absorbed and drawn into the HME foam 1015 and transferred to the absorbent layer 228. The liquid is absorbed by the absorbent layer 228, and is pulled through the holes 247 of the diverter layer 232, thereby spreading the liquid and leading to higher utilization of the absorbent layer 228. In the non-limiting example in which a hydrogel diverter layer, such as diverter layer 545 in FIG. 5, is used in lieu of the diverter layer 232, gel blocking can occur at the holes 247 so that liquid is forced to move around in the absorbent layer 228 and is distributed. The second absorbent layer 1040 further absorbs any liquid flowing through the diverter layer 232 while the second HME layer 1041 manifolds a reduced pressure across the second absorbent layer 1040. In some cases, the second HME layer 1041 may be subjected to compression forces when reduced pressure is applied through the reduced pressure dressing 1000. Despite such compression forces, the second HME layer 1041 may still contain open pressure channels that allow the second HME layer 1041 to transfer reduced pressure to other parts of the reduced pressure dressing 1000. A filter, such as liquid-air separator 240, may be positioned above the HME layer 1041 to restrain or prevent the liquid from leaving the reduced pressure dressing 1000.

Figure 11:
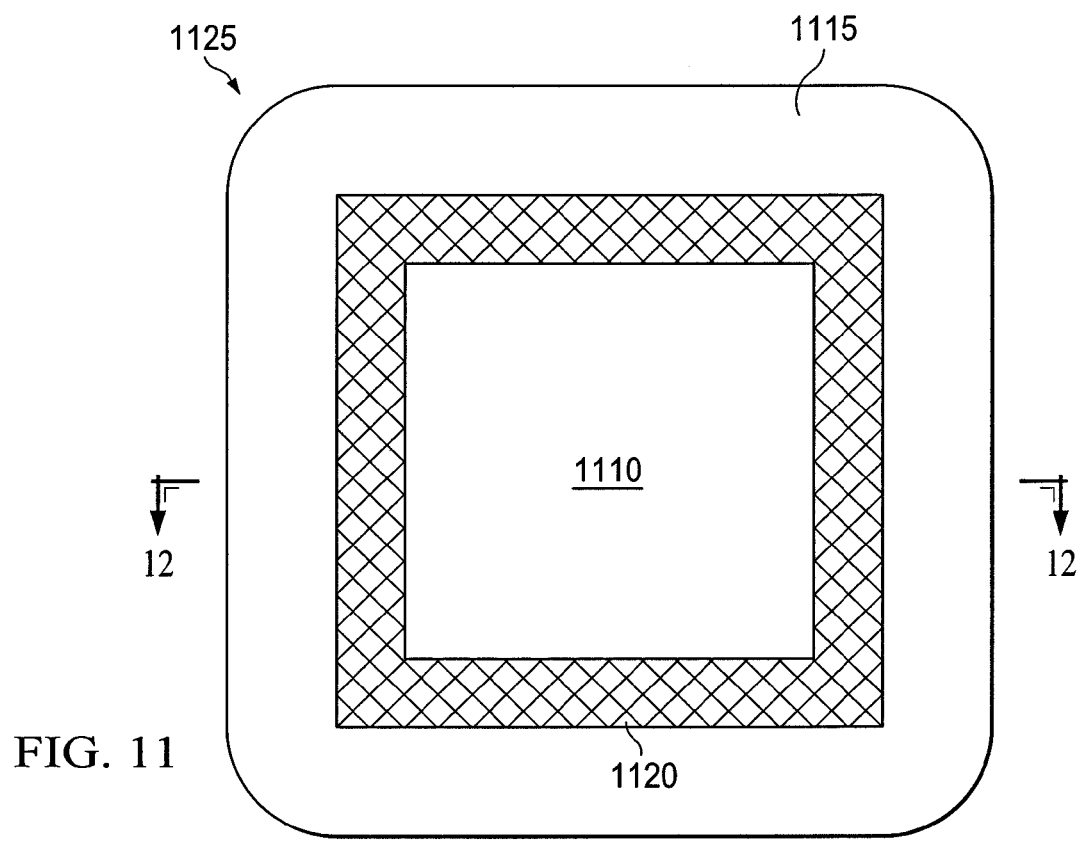
FIG. 11 illustrates a top view of a drape for use with a reduced pressure dressing according to an illustrative embodiment.
Figure 12:
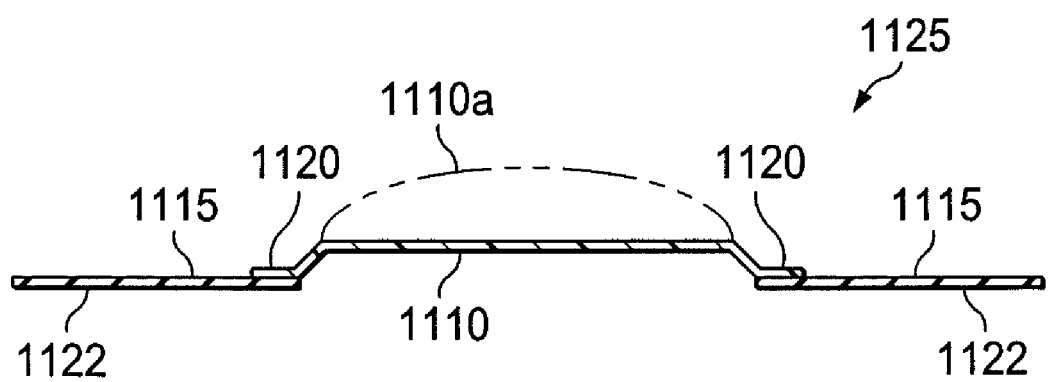
FIG. 12 depicts a cross-sectional front view of the drape of FIG. 11.

Referring to FIGS. 11 and 12, a drape 1125, or cover, is provided that may be used with a reduced pressure dressing such as, for example, reduced pressure dressing 104 of FIGS. 1-3. The drape 1125 includes an elastic portion 1110. The elastic portion 1110 is centrally located on the drape 1125. The elastic portion 1110 may be made from any elastic material. Also, although FIGS. 11 and 12 do not show an aperture on the elastic portion 1110, the elastic portion 1110 may include an aperture, such as the aperture 260 in FIG. 2. The aperture may be located anywhere on the elastic portion 1110. The elastic portion 1110 is bonded to a peripheral portion 1115 at a bonding area 1120. The bond at the bonding area 1120 may be formed using any bonding technique. For example, the elastic portion 1110 may be glued or otherwise adhered to the peripheral portion 1115 at the bonding area 1120.

The peripheral portion 1115 may be made from any material, including an elastic or a non-elastic material. In one example, the peripheral portion 1115 includes an aperture. A tissue facing side 1122 of the peripheral portion 1115 may include an adhesive so that the drape 1125 may be used to cover and secure one or more layers, such as the layers of reduced pressure dressing 104. In another embodiment, both the elastic portion 1110 and the peripheral portion 1115 may be made from the same material and be continuous with one another so that no bond is needed between the elastic portion 1115 and the peripheral portion 1115 at the bonding area 1120.

As illustrated in FIG. 12, the elastic portion 1110 may expand to a plurality of positions, from an unexpanded position shown by the solid line to an expanded position 1110a shown by the broken line. As the reduced pressure dressing with which the drape 1125 is used fills with liquid, the elastic portion 1110 moves to the expanded position 1110a. The ability of the drape 1125 to move to the expanded position 1110a allows for additional room in the reduced pressure dressing for the storage of liquid from the tissue site 108 (not shown).

As an alternative to a drape having an elastic portion, the drape 1125 may instead be made from an inelastic material that is capable of plastically deforming into an expanded position as fluid is collected in a dressing. The drape 1125 may instead include a combination of elastic and inelastic materials, and expansion may be based on both elastic and plastic deformation of the materials.

Figure 13:
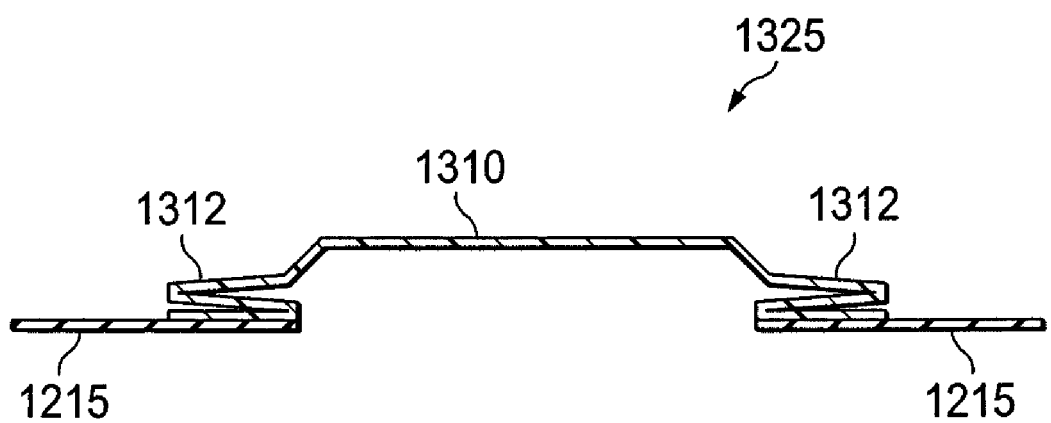
FIG. 13 illustrates a cross-sectional front view of a drape for use with a reduced pressure dressing according to an illustrative embodiment.

Referring to FIG. 13, a drape 1325, or cover, includes a pleated portion 1310 that is centrally located on the drape 1310. The pleated portion 1310 may be made from an elastic or a non-elastic material. The pleated portion 1310 also includes one or more corrugations 1312, or ridges. The corrugations may be located on any or all sides of the pleated portion 1310. Also, although FIG. 13 shows one corrugation on each side of the pleated portion 1310, each side of the pleated portion 1310 may includes any number of corrugations, which may form a bellows-like structure. The pleated construction of the pleated portion 1310 allows the pleated portion 1310 to expand as liquid is stored in an underlying reduced pressure dressing.

The drapes 1125 and 1325 of FIGS. 11-13 are capable of expanding to accommodate fluid collection and storage in a reduced pressure dressing. It is also important to note that the drapes 1125 and 1325 are capable of maintaining reduced pressure in the dressing before, during, and after expansion.

Figure 14:
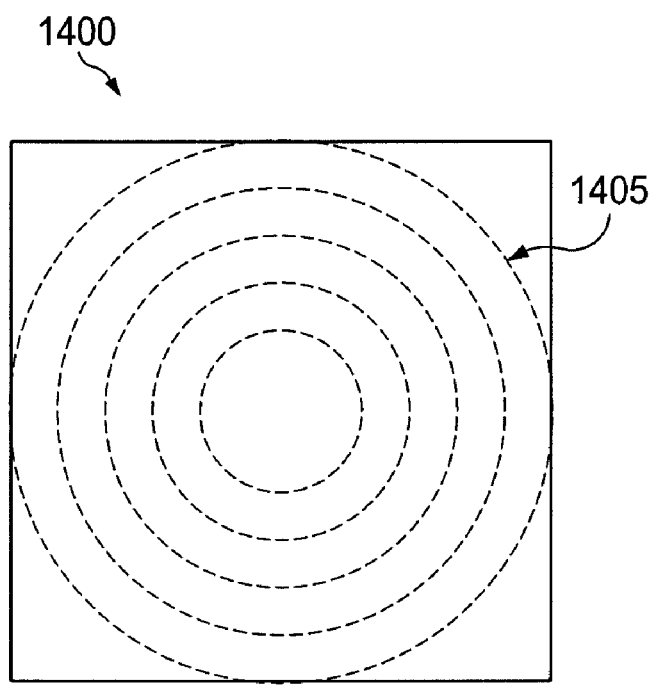
FIG. 14 depicts a top view of a tissue interface layer for use with a reduced pressure dressing according to an illustrative embodiment.
Figure 15:
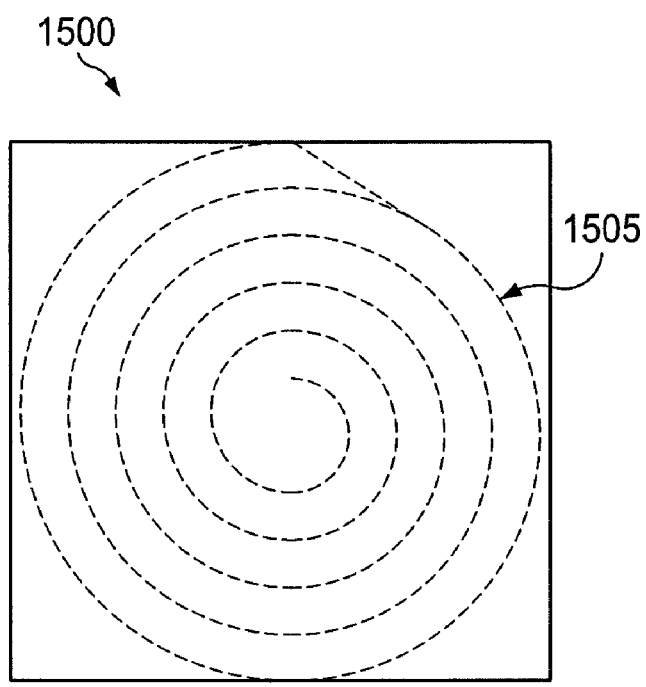
FIG. 15 illustrates a top view of a tissue interface layer for use with a reduced pressure dressing according to an illustrative embodiment.

Referring to FIGS. 14 and 15, interface layers 1400 and 1500 are illustrated according to illustrative embodiments. The interface layers 1400 and 1500 are tearable sheets foam material that include kiss-cut perforations 1405 and 1505 that allow for the easy tearing and sizing of the interface layers 1400 and 1500 for use in a dressing, such as reduced pressure dressing 104. In one example, when the interface layers 1400 and 1500 are kiss-cut, the cutting die penetrates through most of the thickness of the foam material, but not fully. This provides a weakened path to tear along, while still allowing the foam to maintain a shape. In FIG. 14, the kiss-cut perforations 1405 are a series of concentric circles. A properly sized interface layer may be torn along any one of the concentric circles. In FIG. 15, the kiss-cut perforation 1505 is a continuous spiral-like perforation. The kiss-cut perforation 1505 may be torn along this continuous perforation as needed to size the interface layer prior to use with the dressing.

The kiss-cut perforations 1405 and 1505 provide a weakened path along which the interface layer may be torn. When a portion of the interface layers 1400 and 1500 is used in a dressing, the interface layer may still have some perforations remaining. However, despite having these perforations, the interface layer is still able to maintain a desirable shape and effectively perform the functions of the interface layer described herein.

Figure 16:
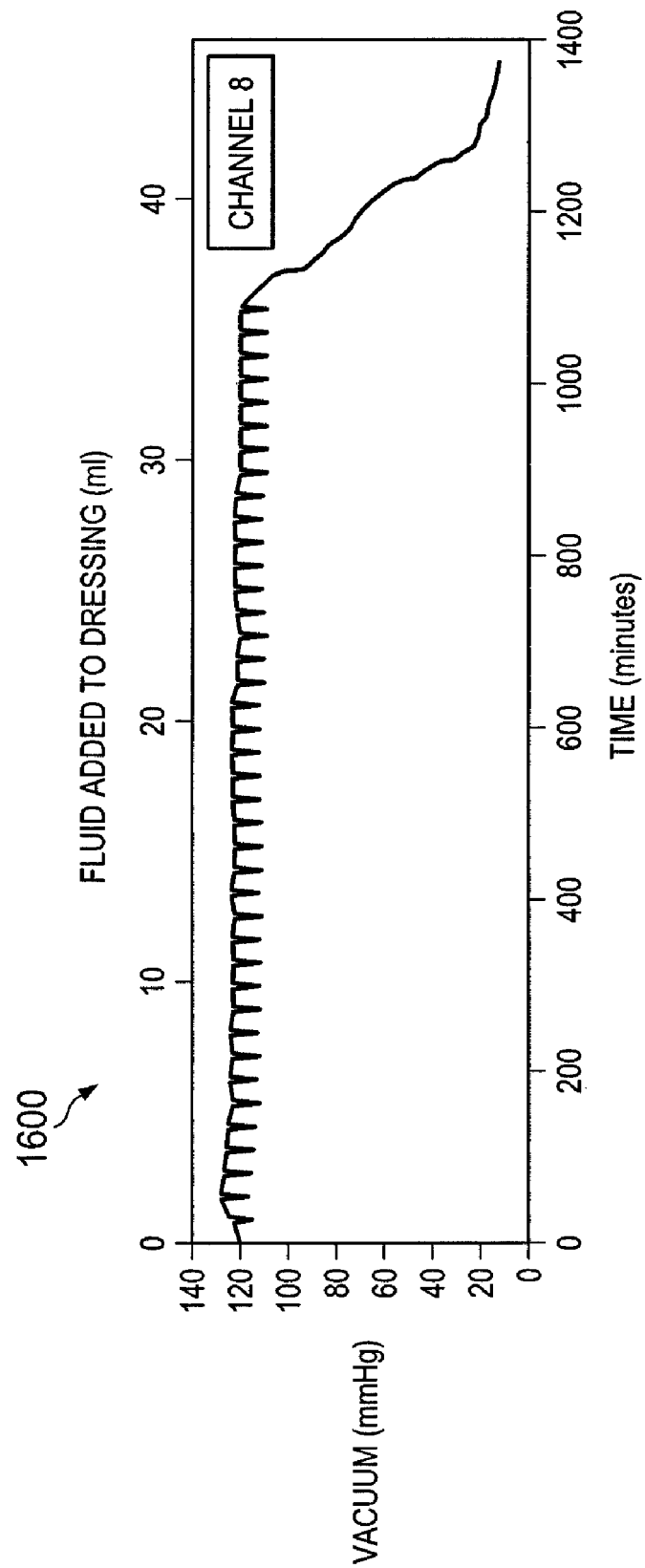
FIG. 16 depicts a graph showing vacuum pressure versus time for a reduced pressure treatment system applying reduced pressure to a tissue site according to an illustrative embodiment.

Referring to FIG. 16, a graph 1600 that shows example characteristics of a reduced pressure dressing is shown. The graph 1600 illustrates a drop in pressure measured as a function of time at an interface layer of a reduced pressure dressing to which fluid is added at about 2 milliliters per hour. In particular, the graph 1600 shows a pressure measured at an interface layer of a dressing that is about 8 $cm^2$ and includes an HME foam with a secondary Super Absorbent Fiber layer dressing mounted on a large tube during the test. The reduced pressure applied to the dressing throughout the test is a consistent 125 mmHg. As time passes and the dressing fills with fluid, the pressure eventually drops at the interface layer as the dressing is no longer able to adequately manifold reduced pressure. The graph 1600 represents characteristics of only one particular reduced pressure dressing, and other illustrative embodiments of the dressing described herein may exhibit different characteristics than those shown in the graph 1600.

Figure 17:
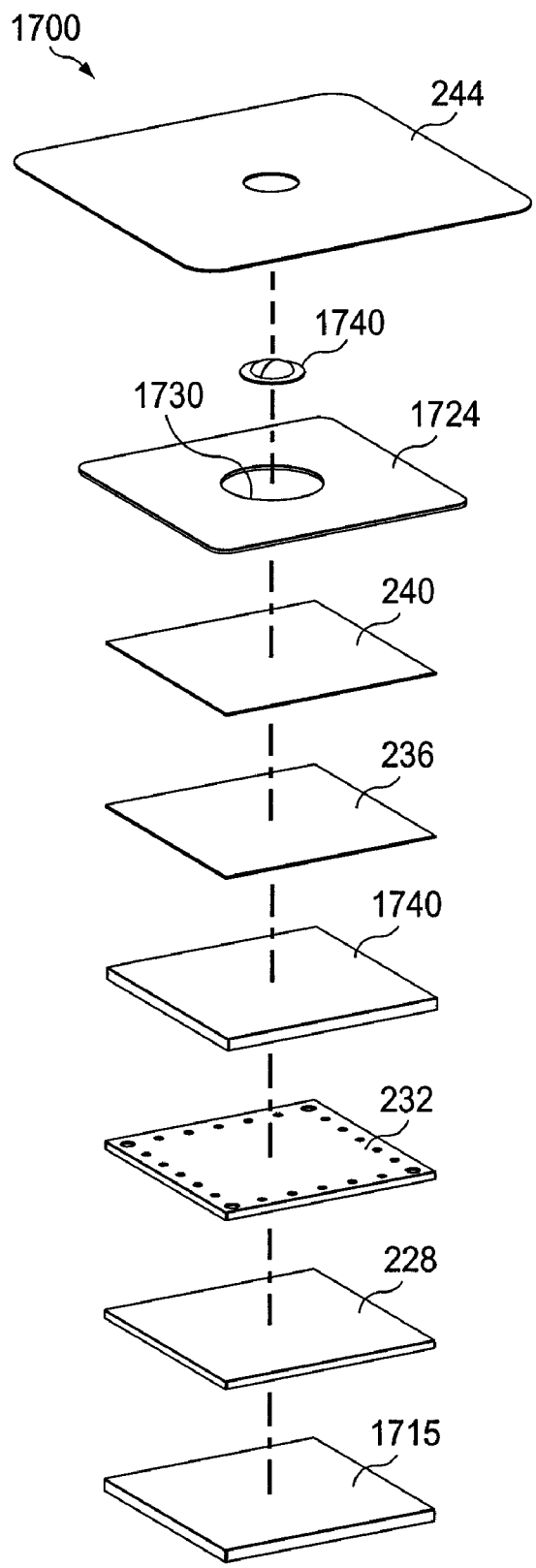
FIG. 17 illustrates an exploded perspective view of a reduced pressure treatment dressing according to an illustrative embodiment.

Referring to FIG. 17, a dressing 1700 according to an illustrative embodiment includes a interface layer 1715. In contrast to the interface layer 220 in FIG. 2, the interface layer 1715 has a larger size relative to the other layers in the dressing. The dressing 1700 includes absorbent layer 228 above the tissue interface layer 1715, and diverter layer 232 above the absorbent layer 228. In contrast to the reduced pressure dressing 104, the dressing 1700 includes another absorbent layer 1740 above the diverter layer 232. The absorbent layer 1740 is similar to the absorbent layer 228. The absorbent layer 1740 may be added to increase the absorbency of the dressing 1700. The absorbent layer 1740 may also be used to catch liquid that travels past or escapes from the absorbent layer 228.

The dressing 1700 includes second manifold layer 236 above the absorbent layer 1740, and liquid-air separator 240 above the second manifold layer 236. The dressing 1700 also includes a seal layer 1724 (similar to the seal layer 222 of FIG. 2) above the liquid-air separator 240. The seal layer 1724 has a circular aperture 1730, although the circular aperture 1730 may be any shape. The dressing 1700 may also include a tubing adapter 1740 and cover 244. The tubing adapter 1740 may be a low-profile dome shape or any other shape.

In one embodiment, the components of the dressing 1700 that are adapted to contact a tissue site are the tissue interface layer 1715, the seal layer 1724, and the cover 244. However, the components of the dressing 1700 may be sized such that any of the components may come into contact with the tissue site.

In another illustrative embodiment, a method is provided for collecting fluid in a dressing positioned at a tissue site. The method includes applying a reduced pressure to the tissue site through the dressing, absorbing liquid from the tissue site, and storing the liquid in the dressing. The method further includes preventing the liquid from exiting the dressing. In one embodiment, the step of absorbing liquid from the tissue site is accomplished with an absorbent layer similar to the absorbent layers described herein. The method may further comprise diverting reduced pressure to a target region of the absorbent layer to increase an absorption efficiency associated with the absorbent layer. Diversion of the reduced pressure to the target region may also increase an amount of time that the absorbent layer is able to distribute reduced pressure.

The illustrative embodiments of reduced pressure dressings described herein may contain a diverter layer to ensure that even pressure distribution is maintained as an absorbent layer absorbs fluid. The diverter layer also promotes the efficient use of the absorbent material in the dressing. The illustrative embodiments may also contain a porous hydrophobic filter that prevents the dressing from allowing liquid, such as exudate, from entering a tubing and helping to ensure pressure distribution. The construction of the dressing and the sequence of layers in the illustrative embodiments helps to ensure the optimal absorbency of the dressing combined with the communication of reduced pressure to the tissue site.

Current wound dressings are designed to absorb liquid to maintain a moist wound environment while minimizing the risk of maceration, but are unsuited to adequately manifold reduced pressure. Current dressings that are not currently used with reduced pressure will not normally transmit pressure to a tissue site. These current dressings are designed only to absorb fluid and are routinely changed. The dressings described in the illustrative embodiments are adapted to provide therapy and more absorbent capacity both with and without reduced pressure, and may be applied to a large variety of wounds, including low-severity wounds and low-exudating wounds. The dressings described in the illustrative embodiments will allow reduced pressure tissue therapy without impacting the dressings' absorbency.

Without the diversion provided by components such as the diverter layer, liquid may be absorbed by the absorbent layer and concentrated into a restricted area around the point of exudation. This may lead to large amounts of the absorbent layer being unused. For example, when a reduced pressure source of 125 mmHg is connected to a reduced pressure dressing, the absorbent material may release some of the absorbed liquid, which will bypass the rest of the absorbent area and be drawn directly into the tube that connects the reduced pressure source to the dressing. At this point, the dressing may cease to absorb any more liquid, and as the liquid enters the tube, the dressing's ability to transmit reduced pressure to the tissue site is impaired. Furthermore, this may occur when only a fraction of the target fluid quantity has been absorbed. However, by using a diverter layer and other layers described herein, the efficiency of the absorbent layers may be increased so that the reduced pressure dressing is capable of absorbing more liquid and manifolding reduced pressure for a longer period of time.

The components of the reduced pressure dressings described herein are illustrated in a non-limiting spatial configuration that may be altered depending on the implementation. Although the figures show components of the reduced pressure dressings in a particular order, the components may have any order depending on the implementation. Similarly, the inclusion or exclusion of any particular component may vary depending on the particular application.

Dressing with Integrated Pump

The reduced pressure dressings and components in FIGS. 1-17 have been described as being adapted for connection to a reduced pressure source external to the dressing. However, the reduced pressure dressings described herein are also capable of incorporating an integrated pump, i.e. a pump positioned within or between layers of the dressing, to deliver reduced pressure through the layers of the dressing to the tissue site.

Figure 18:
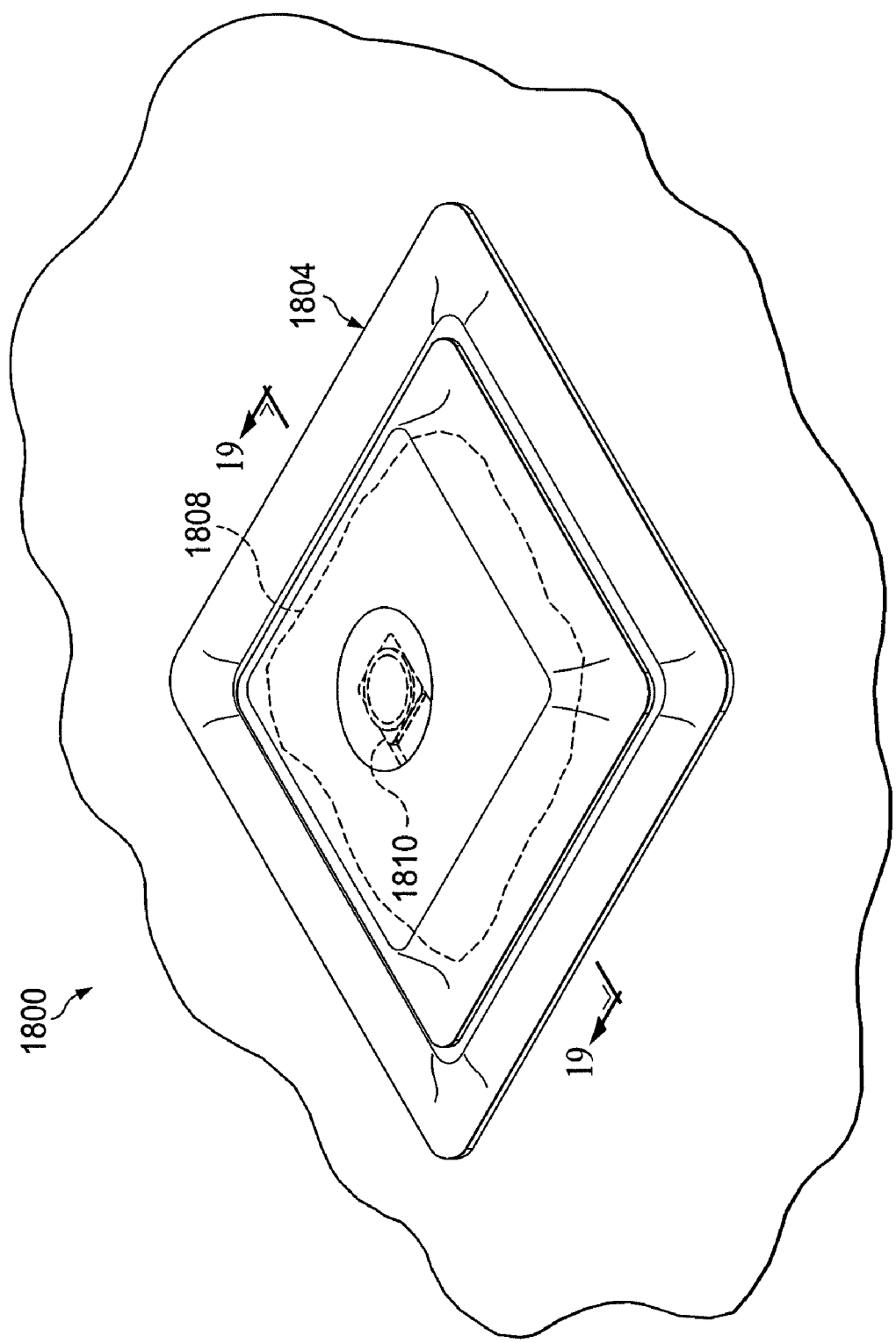
FIG. 18 depicts a perspective view of a reduced pressure treatment system according to an illustrative embodiment, the reduced pressure treatment system having a dressing with an integrated pump positioned at a tissue site.

Referring to FIG. 18, a reduced pressure treatment system 1800 according to an illustrative embodiment includes a reduced pressure dressing 1804 positioned at a tissue site 1808 of a patient. The reduced pressure dressing 1804 includes a reduced pressure pump 1810 that is integrated into the reduced pressure dressing 1804. In addition to the reduced pressure pump 1810, other components may also be integrated into the dressing, including without limitation sensors, processing units, control units, alarm indicators, memory, databases, software. Additionally, the reduced pressure dressing 1804 may include interfaces (wireless or wired) that allow fluid communication between components within the dressing 1804 and components that may be outside of the dressing 1804. In one non-limiting example, the interface may be a USB port. The external components may include without limitation control units, display units, battery chargers, and user interfaces that further facilitate the application of reduced pressure treatment to the tissue site 1808. Delivery of reduced pressure to the reduced pressure dressing 1804 and tissue site 1808 by the reduced pressure pump 1810 encourages new tissue growth by maintaining drainage of exudate from the tissue site, increasing blood flow to tissues surrounding the tissue site, and creating microstrain at the tissue site.

Figure 19:
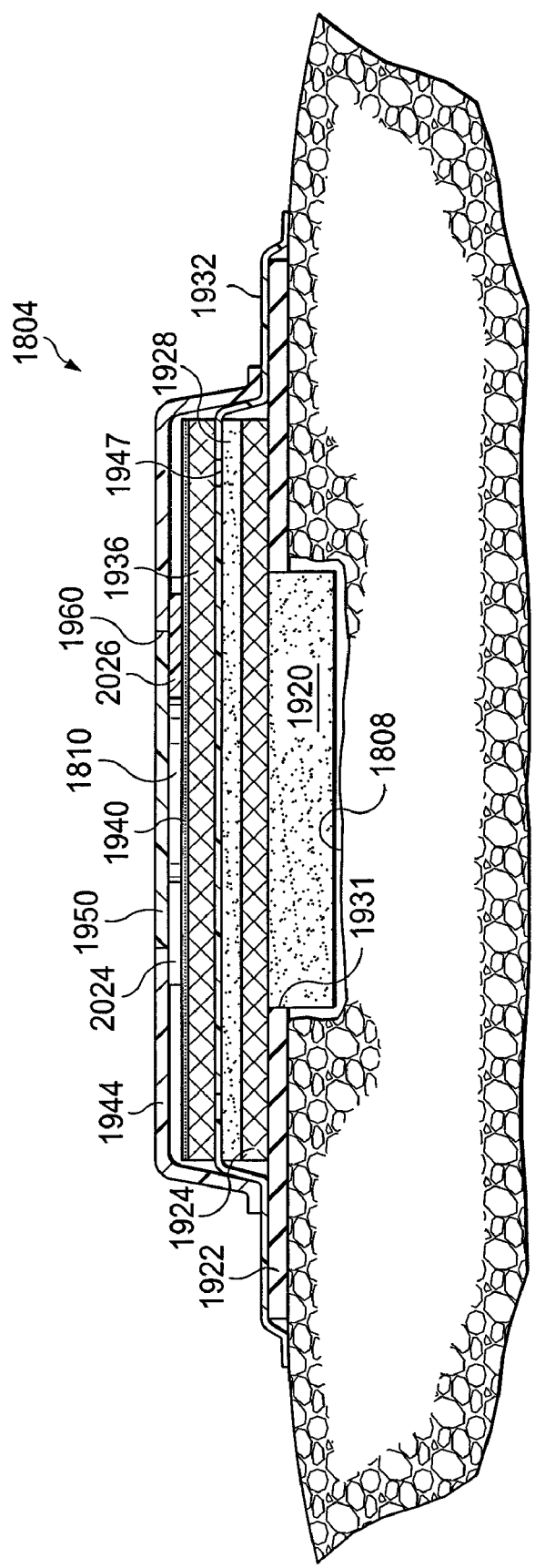
FIG. 19 illustrates a cross-sectional front view of the dressing and pump of FIG. 18 taken at 19-19.
Figure 20:
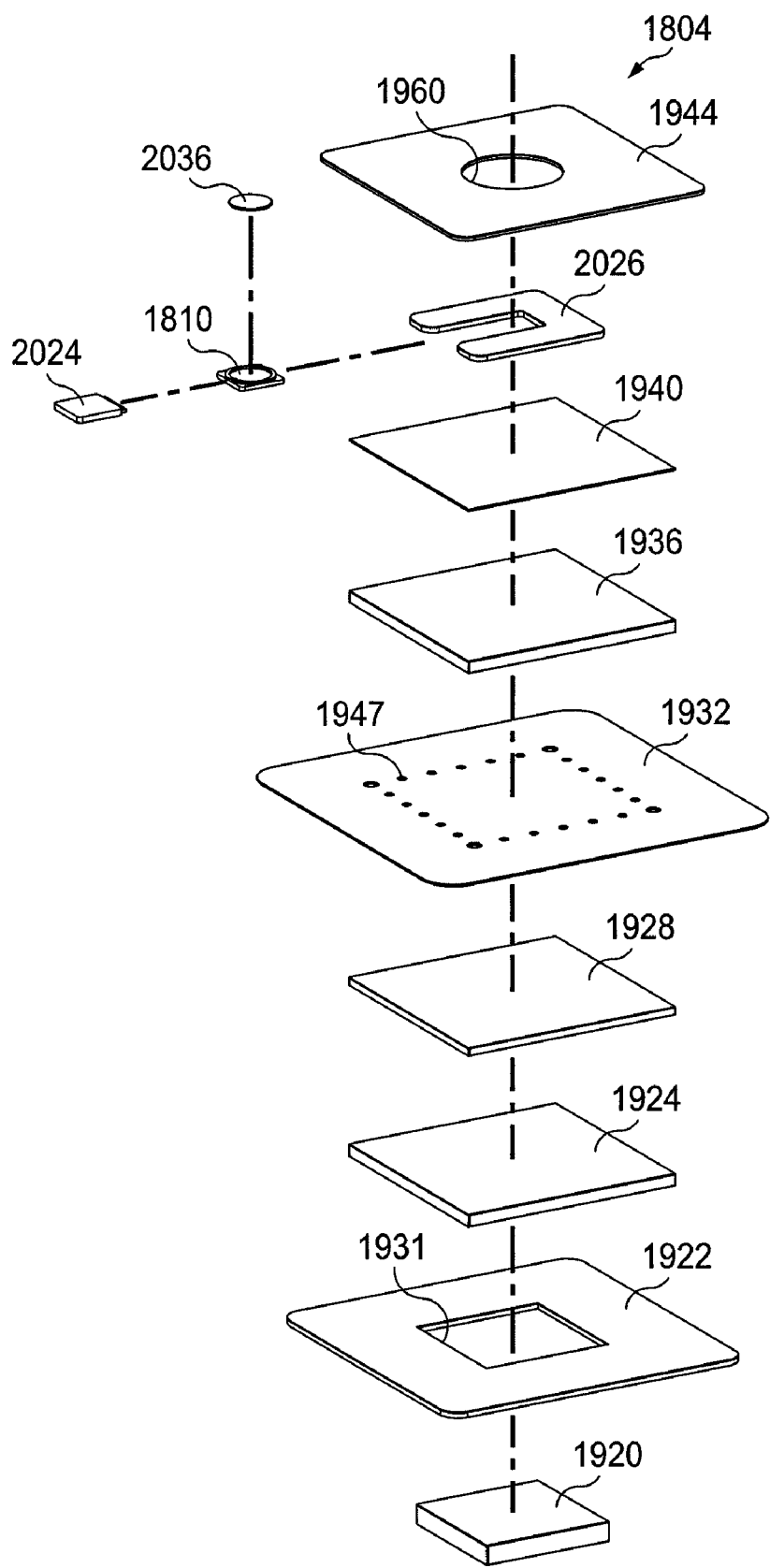
FIG. 20 depicts an exploded perspective view of the dressing and pump of FIG. 18.

Referring to FIGS. 19 and 20, the reduced pressure dressing 1804 includes an interface layer 1920 adapted to be positioned at the tissue site 1808, and a seal layer 1922 to seal the reduced pressure dressing 1804 around the tissue site 1808. A first manifold layer 1924 is positioned in fluid communication with the interface layer 1920 to distribute the reduced pressure to the interface layer 1920 and the tissue site 1808. An absorbent layer 1928 is positioned in fluid communication with the first manifold layer 1924 to absorb liquid from at least one of the first manifold layer 1924, the interface layer 1920, and the tissue site 1808. A diverter layer 1932 positioned adjacent the absorbent layer 1928. A second manifold layer 1936 is positioned in fluid communication with the diverter layer 1932, and a liquid-air separator 1940 is positioned adjacent the second manifold layer 1936. A cover 1944, or drape, is positioned adjacent the second liquid-air separator 1940. An indicator and odor filter may also be positioned within the reduced pressure dressing 1804.

The multiple layers of reduced pressure dressing 1804 are similar in shape, size, positioning, and function to the layers of any of the other reduced pressure dressings described herein. In addition to the layers of dressing 1804 listed above, the reduced pressure dressing 1804 includes a pump 1810 that may be integrated into the dressing between the liquid-air separator 1940 and the cover 1944. The pump 1810 may be a micropump that is small and light enough such that the integrated reduced pressure dressing 1804 is able to be maintained on the tissue site 1808. Furthermore, the size and weight of the pump 1810 should be such that the integrated reduced pressure dressing 1804 does not pull or otherwise adversely affect the tissue site 1808. In one embodiment, the pump 1810 may be a disk pump having a piezoelectric actuator similar to that described in International Patent Application No. PCT/GB2006/001487, published as WO 2006/111775, which is hereby incorporated by reference. In an alternative embodiment, the pump 1810 may be a peristaltic pump that is used for pumping a variety of fluids. It should be understood that alternative pump technologies may be utilized and that rotary, linear, or other configurations of pumps may be utilized.

The pump 1810 may be used to create enough reduced pressure to be "therapeutic" for wound therapy. In one embodiment, the pump 1810 has sufficient flow, vacuum, and operation life characteristics to enable continuous application of reduced pressure treatment. The flow may range between about 5-1000 ml/min, the vacuum may range between about 50-200 mmHg, and continuous operating life may last greater than 20 hours. It should be understood that alternative ranges may be utilized depending on the configuration of the integrated reduced pressure dressing 1804, size of wound, type of wound, or otherwise. In one embodiment, multiple pumps may be positioned in a single dressing to deliver increased flow rates or vacuum levels as required. Alternatively, a selection of pumps having different operational capabilities and specifications may be kept on hand by a user or medical practitioner to allow optimization of a pump and dressing combination for a particular tissue site.

The pump 1810 is disposed within the dressing to avoid conduits and external canisters for collection of wound exudate. The pump 1810 may include a valve 1950 or outlet port to release air or exhaust out of the reduced pressure dressing 1804. If valve 1950 is used, the valve 1950 may be in fluid communication with, or may be positioned within, an aperture 1960 of the cover 1944. Alternatively, the cover 1944 may be sealed around an outlet port of the pump 1810 such that gas from the pump 1810 is able to exhaust directly through the aperture 1960. In the embodiment illustrated in FIGS. 18-20, the valve or outlet port of the pump 1810 is oriented in a direction away from the hydrophobic filter to avoid adding air to the wound dressing. The air exhausts through an aperture 1960 in the cover 1944, which may include a one-way valve. Alternatively, the air or other gas could be exhausted through a gas-permeable portion of the cover 1944 as long as the ability of the cover 1944 to maintain reduced pressure is not affected.

When a piezoelectric-driven pump is used in a dressing, the piezoelectric actuator associated with the pump may be driven at different frequencies to act as a buzzer or vibrating alert system. The alert system may be used to alert a user to an alarm condition such as the presence of a leak in the dressing, a change in reduced pressure as measured by a sensor, an indication that the dressing has absorbed a maximum capacity of liquid as may be indicated by an indicator, or an indication that one or more layer are no longer manifolding reduced pressure efficiently.

Control electronics 2024 may be utilized to control operation of the pump 1810. The control electronics 2024 may be analog and/or digital and be configured with a regulator (not shown) to regulate speed or duty cycle at which the pump 1810 operates. Furthermore, the control electronics 2024 may be configured with a controller (not shown) that receives sense signals from sensors or switches (not shown). The sensors may be disposed throughout the integrated reduced pressure dressing 1804 to sense parameters, such as pressure, temperature, moisture, chemistry, odor, or any other parameter that may be utilized in managing and controlling the pump 1810. In one embodiment, the control electronics 2024 include a computer processor. Alternatively, the control electronics 2024 may include a programmable gate array. Still yet, the control electronics 2024 may be formed of analog electronic components. It should be understood that the control electronics 2024 may include any form of digital and/or analog components to perform functionality as described herein.

As understood in the art, there are four basic parameters that are of concern when performing reduced pressure wound treatment, including (i) low pressure, (ii) excessive leak, (iii) level of absorbent layer, and (iv) battery state. Accordingly, the control electronics 2024 may include electronics that may be utilized to monitor each of the four basic parameters and generate an alarm signal (e.g., high-pitched beep, vibration, or light) using a speaker (not shown), vibrator (not shown), or illumination device (not shown), such as a light emitting diode (LED), to notify a medical professional, patient, or family member that a parameter is outside of a safe range. For example, if a pressure at the wound site is below a therapeutic level, a continuous tone may be generated. As another example, if the absorbent layer 1928 is saturated, then continuous beeps may be generated. Still yet, if the battery drops below a certain voltage level, then a different frequency may be generated and/or LED may be turned on. A variety of different alarm signals may be established to notify a medical professional to take a particular action.

A battery 2026 may be utilized to provide electric power to the pump 1810 and control electronics 2024. The battery 2026 may have any size and shape configuration and be of any material, such as polymer, to accommodate weight and size of the integrated reduced pressure dressing 1804, as previously described. In one embodiment, the battery 2026 may be rechargeable. In another embodiment, the battery 2026 may be disposed within or outside of the integrated reduced pressure dressing 1804 and be positioned in such a manner as to allow for easy replacement or recharging. In one embodiment, the battery 2026 may be configured with a voltage level sensor (not shown) that is monitored by the control electronics 2024 for determination of a low power level. In one embodiment, the battery 2026 may be directly connected with the pump 1810. Alternatively, the battery 2026 may be connected to the control electronics 2024 that use power from the battery 2026 to drive the pump 1810. The control electronics 2024 may provide continuous power, modulated power, such as a pulsewidth modulated (PWM) signal, to drive the pump 1810.

The seal layer 1922 may be adhered to or otherwise connected to the cover layer 1944 that is used to drape or otherwise cover the integrated reduced pressure dressing 1804. The seal layer 1922 may include an aggressive or medical grade adhesive material that is strong enough to form a vacuum seal with skin around a wound of a patient. The seal layer 1922 may be a band that has an opening 2032 that is slightly larger than the geometric parameters as the hydrophobic filter 2020 or other layer so that the cover layer 2030 may contact skin around the wound site of a patient. The cover layer 2030 may be impermeable to fluids, such as air and liquids. In one embodiment, the cover layer 2030 includes a valve 2034 to enable exhaust from the pump 1810 to be discharged from the integrated reduced pressure dressing 1804. The valve 2034 may be a one-way valve to minimize fluids from entering into the integrated reduced pressure dressing 1804 via the cover layer 2030.

In another embodiment, the seal layer 1922 may be adhered to the diverter layer 1932 and the diverter layer 1932 adhered to the cover 1944 to create an upper dressing portion and a lower dressing portion. The upper dressing portion may include the cover 1944, the pump 1810 and related components, the liquid-air separator 1940, the second manifold layer 1936, and the diverter layer 1932. The lower dressing portion may include the absorbent layer 1928, the first manifold layer 1924, the seal layer 1922, and the interface layer 1920. In one embodiment, the reduced pressure dressing may be configured to allow replacement of the lower dressing portion once the dressing has absorbed a maximum capacity of fluid. The upper dressing portion may be reused after the lower dressing portion is replaced. This allows multiple use of the pump 1810, while disposable portions of the dressing may be replaced. In another embodiment, the pump 1810, control electronics 2024, and battery 2026 may be removed from the dressing for reuse and the remaining layers of the dressing replaced. In still another embodiment, the absorbent layer 1928 only may be replaced. In yet another embodiment, the absorbent layer 1928 and the interface layer 1920 only may be replaced.

A charcoal filter 2036 may be utilized in the integrated reduced pressure dressing 1804 to reduce odors created by the wound site and dispersed from the integrated reduced pressure dressing 1804. The charcoal filter 2036 may be disposed above a valve or other output vent from the pump 1810 to filter exhaust from the pump 1810 prior to being released from the integrated reduced pressure dressing 1804. It should be understood that the charcoal filter 2036 may be alternatively configured and disposed above or below the pump 1810. Still yet, rather than using a charcoal filter, charcoal may be integrated into any or all of the different layers utilized in the integrated reduced pressure dressing 1804.

In another illustrative embodiment, a method for collecting liquid in a dressing positioned at a tissue site includes generating a reduced pressure using a pump positioned within the dressing. A liquid is absorbed from the tissue site and is stored in the dressing. The liquid is prevented from entering the pump. The method may further include maintaining the reduced pressure within the dressing and exhausting gas from the pump outside the dressing.

It should be apparent from the foregoing that an invention having significant advantages has been provided. While the invention is shown in only a few of its forms, it is not just limited but is susceptible to various changes and modifications without departing from the spirit thereof.

We claim:

1. A reduced pressure treatment system comprising:
a reduced pressure source; and
a dressing comprising:
an interface layer adapted to be positioned at a tissue site;
an absorbent layer in fluid communication with the interface layer to absorb liquid from at least one of the interface layer and the tissue site, the absorbent layer having a perimeter region and a center region;
a diverter layer formed from a substantially liquid-impermeable material and positioned between the absorbent layer and the reduced pressure source, the diverter layer including a plurality of apertures in fluid communication with the absorbent layer to distribute a reduced pressure to the absorbent layer, the apertures positioned on the diverter layer substantially within the perimeter region of the absorbent layer and away from the center region of the absorbent layer;
a cover positioned over the diverter layer to maintain the reduced pressure at the tissue site; and
wherein a surface area of the diverter layer is greater than a surface area of the cover; and
wherein the reduced pressure source is located external to the dressing and fluidly coupled to the dressing.

2. The reduced pressure treatment system of claim 1, wherein the interface layer is hydrophobic.

3. The reduced pressure treatment system of claim 1, wherein the absorbent layer includes a super absorbent fiber.

4. The reduced pressure treatment system of claim 1 further comprising a liquid-air separator positioned between the absorbent layer and the cover.

5. The reduced pressure treatment system of claim 1 further comprising:
a liquid-air separator positioned between the absorbent layer and the cover; and
wherein at least a portion of the cover is adhesively coupled to the diverter layer and at least a portion of the diverter layer is configured to be coupled to a tissue surrounding the tissue site.

6. The reduced pressure treatment system of claim 5 further comprising a seal layer configured to be positioned between the diverter layer and the tissue surrounding the tissue site.

7. The reduced pressure treatment system of claim 1, wherein the reduced pressure source is a manually-actuated pump.

8. The reduced pressure treatment system of claim 1, wherein the apertures of the diverter layer are positioned near at least one perimeter edge of the diverter layer.

9. The reduced pressure treatment system of claim 1, wherein at least one of the apertures is larger than another of the apertures.

10. The reduced pressure treatment system of claim 1, wherein at least one of the apertures is configured to become smaller on contact with moisture.

11. The reduced pressure treatment system of claim 1, wherein the diverter layer includes a plurality of ridges on a surface of the diverter layer to define a plurality of channels between the ridges.

12. The reduced pressure treatment system of claim 1, wherein the diverter layer allows the absorption capabilities of the absorbent layer to be more fully utilized.

13. The reduced pressure treatment system of claim 1, wherein the diverter layer increases an amount of time over which the absorbent layer is capable of distributing reduced pressure.

14. The reduced pressure treatment system of claim 1, wherein the diverter layer is gas permeable.

15. A reduced pressure treatment system comprising:
a reduced pressure source; and
a dressing comprising:
an interface layer adapted to be positioned at a tissue site;
an absorbent layer in fluid communication with the interface layer to absorb liquid from at least one of the interface layer and the tissue site, the absorbent layer having a perimeter region and a center region;
a diverter layer formed from a substantially liquid-impermeable material and positioned between the absorbent layer and the reduced pressure source, the diverter layer including a plurality of apertures in fluid communication with the absorbent layer to distribute a reduced pressure to the absorbent layer, the apertures positioned on the diverter layer such that the reduced pressure is applied to the absorbent layer to direct the liquid radially outward from the center region to the perimeter region;

a cover positioned over the diverter layer to maintain the reduced pressure at the tissue site; and wherein a surface area of the diverter layer is greater than a surface area of the cover; and wherein the reduced pressure source is located external to the dressing and fluidly coupled to the dressing.

* * * * *

UNITED STATES PATENT AND TRADEMARK OFFICE
CERTIFICATE OF CORRECTION

PATENT NO. : 8,372,049 B2
APPLICATION NO. : 12/398891
DATED : February 12, 2013
INVENTOR(S) : Jonathan Paul Jaeb et al.

It is certified that error appears in the above-identified patent and that said Letters Patent is hereby corrected as shown below:

On the Title page, (75) Inventors: please change "Aldan Marcus Tout, Ringwood (GB)" to correctly be --Aidan Marcus Tout, Ringwood (GB)--.

Signed and Sealed this
Seventeenth Day of June, 2014

Michelle K. Lee
*Deputy Director of the United States Patent and Trademark Office*